United States Patent [19]

Alvarez

[11] 4,273,770
[45] Jun. 16, 1981

[54] 4-HALO STEROIDS

[75] Inventor: Francisco S. Alvarez, Sunnyvale, Calif.

[73] Assignee: Syntex (U.S.A.) Inc., Palo Alto, Calif.

[21] Appl. No.: 67,984

[22] Filed: Aug. 20, 1979

Related U.S. Application Data

[63] Continuation-in-part of Ser. No. 893,641, Apr. 5, 1978, abandoned.

[51] Int. Cl.³ .............................................. C07J 5/00
[52] U.S. Cl. ........................... 424/241; 260/239.55 D; 260/239.5; 260/397.45; 260/239.55 R; 424/243
[58] Field of Search .................. 260/397.45, 239.55 D

[56] References Cited

U.S. PATENT DOCUMENTS

| | | | |
|---|---|---|---|
| 2,897,199 | 7/1959 | Ringold et al. | 260/397.45 |
| 3,489,748 | 1/1970 | Els et al. | 260/239.55 |

FOREIGN PATENT DOCUMENTS

| | | | |
|---|---|---|---|
| 895400 | 5/1962 | United Kingdom | 260/239.55 D |
| 1211220 | 4/1970 | United Kingdom | 260/239.55 |

*Primary Examiner*—Elbert L. Roberts
*Attorney, Agent, or Firm*—Kate H. Murashige; Tom M. Moran; Alan M. Krubiner

[57] ABSTRACT

Certain pregn-4-ene-3,20-diones or pregn-1,4-diene-3,20-diones 4-substituted with a fluoro or chloro are useful as topical anti-inflammatory steroids. These compounds are substituted at 9α with hydrogen, fluoro, chloro or bromo; at 6α with hydrogen, fluoro or chloro; at the 11 position with a keto, a β-hydroxy or a β-chloro (the latter only when there is a 9α-chloro); at 16α, 17α-positions with isopropylidenedioxy or at 16α- (or 16β) with methyl when 17α is hydroxy (or an ester); and at the 21-position with mono-fluoro, chloro, bromo, hydroxy or alkanoyloxy of 2-6 carbons or difluoro, dichloro, dihydroxy or dimethoxy.

54 Claims, No Drawings

4-HALO STEROIDS

This is a continuation-in-part of application Ser. No. 893,641, filed Apr. 5, 1978, now abandoned.

BACKGROUND OF THE INVENTION

1. Field of the Invention

This invention relates to novel corticosteroids. More specifically it relates to pregn-4-enes which are substituted at the 4 position with fluoro or chloro and are optionally substituted at C-6 with fluoro or chloro. The compounds are topically active anti-inflammatory agents in mammals. The invention further relates to pharmaceutically active compositions comprising the compound of the invention in combination with at least one pharmaceutically acceptable excipient.

2. Prior Art

4-Chlorohydrocortisone and 4-fluorohydrocortisone are known compounds. However, no biological activity is shown for these compounds. See Ernst Jucher, Process in Drug Research, Vol. 5, p. 50, Birkhauser Verlag Basel and Stuttart, 1963. Other chemically related compounds are disclosed in U.S. Pat. No. 2,714,601 to Fonken et al.; U.S. Pat. No. 3,127,424 to Adams et al; and U.S. Pat. No. 3,129,219 to Goly as being useful as intermediates. U.S. Pat. No. 3,232,960 to Magerlein et al discloses certain 4-fluoro-4-pregnenes which may also have double bonds at C-1 and C-6 which are useful as anti-inflammatories.

U.S. Pat. No. 3,192,301 to Westerhof discloses a process for making certain steroids. At column 3 of the patent the broad formula indicates that the patent relates to compounds of the general formula

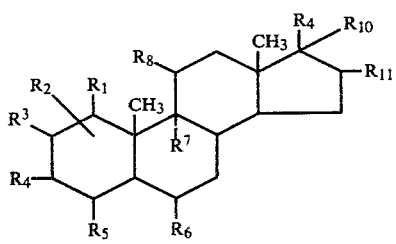

wherein $R^5$ and $R^6$ may be, i.a., halogen. However, the patent does not disclose the preparation of any 4,6α-dihalo steroids.

U.S. Pat. No. 3,707,537 to Kierstead discloses certain 4-chloro-6-halo-pregna-4,6-dienes which require the presence of a 6-7 double bond. Another patent which discloses the possibility of certain 4,6-dihalo-pregna-4-enes is U.S. Pat. No. 3,489,748 to Benningen and Muller. These compounds differ from the compounds of this invention in that the Benningen et al compounds exhibit a 16α-alkylthio group and have no substitution at the 17α position. Furthermore, there are no di-substituted compounds disclosed, only 4-chloro-pregna-4,6,16-triene-3,20-dione and the corresponding 16α-ethylthiopregna-4,6-diene.

Other 3-keto-$\Delta^4$ steroids are also known which are 6,6-difluoro substituted. See, for example, U.S. Pat. No. 3,219,673; U.S. Pat. No. 3,767,684; U.S. Pat. No. 3,822,253; U.S. Pat. No. 3,681,338; U.S. Pat. No. 3,718,673; U.S. Pat. No. 3,546,215; and U.S. Pat. No. 3,629,242.

A heretofore unknown series of compounds has now been disclovered which show high topical anti-inflammatory activity.

SUMMARY OF THE INVENTION

The broadest aspect of this invention is a compound chosen from those represented by the formula

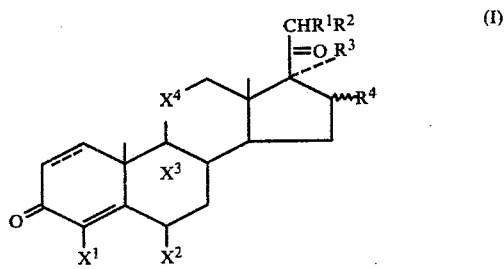

wherein $X^1$ is fluoro or chloro;

$X^2$ is hydrogen, fluoro or chloro;

$X^3$ is hydrogen, fluoro, chloro or bromo;

$X^4$ is =C=O or

or may be

when $X^3$ is chloro;

$R^1$ is hydrogen, fluoro, chloro, bromo, hydroxy or methoxy;

$R^2$ is fluoro, chloro, bromo, hydroxy or alkanoyloxy of 2 through 6 carbon atoms when $R^1$ is hydrogen or $R^2$ is the same as $R^1$ when $R^1$ is fluoro, chloro, hydroxy or methoxy;

$R^3$ is hydroxy or alkanoyloxy of 2 through 6 carbon atoms when $R^4$ is α-methyl or β-methyl or $R^3$ and $R^4$ together are

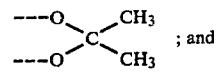

and the solid and broken lines between the 1 and 2 positions in the A ring of the steroid nucleus represent a single or double bond.

Another aspect of this invention is a topical anti-inflammatory pharmaceutical composition which comprises at least one suitable pharmaceutical excipient in combination with a compound chosen from those represented by Formula (I), above, wherein each of the substituents are as defined. Particularly valuable compounds in this composition are set forth herefter.

Still another aspect of this invention is a process for treating an inflamed condition in a mammal which comprises administering a therapeutically effective amount of a compound chosen from those represented by Formula (I), above, wherein the substituents are as defined.

DETAILED DESCRIPTION AND PREFERRED EMBODIMENTS

One subgroup of the broadest aspect of this invention comprises those compounds represented by Formula (I) wherein $X^1$ is fluoro or chloro; $X^2$ is hydrogen or fluoro; $X^3$ is hydrogen or fluoro; $X^4$ is

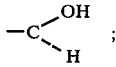

$R^1$ is hydrogen, hydroxy or methoxy; $R^2$ is the same as $R^1$ when $R^1$ is methoxy or hydroxy or is hydroxy, fluoro, chloro or alkanoyloxy of 2–6 carbon atoms when $R^1$ is hydrogen; and $R^3$ and $R^4$ together are 16α,17α-isopropylidenedioxy.

Still another subgroup of this invention comprises the compounds represented by Formula (I) wherein $X^1$ is fluoro or chloro; $X^2$ is hydrogen or fluoro; $X^3$ is hydrogen, chloro or fluoro; $X^4$ is

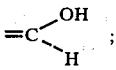

$R^1$ is hydrogen, hydroxy or methoxy; $R^2$ is chloro, fluoro, hydroxy, methoxy or alkanoyloxy of 2–6 carbon atoms, when $R^1$ is hydrogen or $R^2$ is the same as $R^1$ when $R^1$ is hydroxy or methoxy; $R^3$ is hydroxy or alkanoyloxy of 2–6 carbon atoms; and $R^4$ is α-methyl or β-methyl. A subdivision of this subgroup comprises the compounds represented by Formula (I) wherein $R^3$ is hydrogen and $R^2$ is fluoro, chloro, hydroxy or alkanoyloxy of 2–6 carbon atoms; and $R^4$ is α-methyl or β-methyl.

In each of the subgroup of steroids of the 16α-methyl or 16β-methyl series a preferred subgroup includes the compounds represented by Formula (I) wherein $X^1$ is fluoro; $X^2$ is fluoro or hydrogen; $X^3$ is fluoro, chloro or hydrogen; $X^4$ is

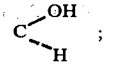

$R^1$ is hydrogen or methoxy; $R^2$ is methoxy when $R^1$ is methoxy or $R^2$ is hydroxy, alkanoyloxy of 2–6 carbon atoms or chloro when $R^1$ is hydrogen; and $R^3$ is hydroxy or alkanoyloxy of 2–6 carbon atoms.

Preferably, in each of the subgroups set forth hereinbefore there is a double bond between C-1 and C-2 of the steroid ring.

In naming the compounds of this invention the first substituent will be the 4-position and all other substituents on the steroid ring shall be included numerically unless there is a substituent the same as that at the 4-position. For example, when $X^1$ is chloro, $X^2$ and $X^3$ are fluoro, $X^4$ is hydroxy, $R^1$ is hydrogen, $R^2$ is methoxy, $R^3$ and $R^4$ together are 16α,17α-isopropylidenedioxy and there is a double bond between C-1 and C-2, the name is 4-chloro-6α,9α-difluoro-11β-hydroxy-16α,17α-isopropylidenedioxy-21-methoxypregna-1,4-diene-3,20-dione. If on the other hand, $R^3$ is hydroxy and $R^4$ is α-methyl while $R^1$, $R^2$ and $X^1$-$X^4$ are the same as immediately named above, the compound is named 4-chloro-6α,9α-difluoro-11β,17α-dihydroxy-16α-methyl-21-methoxypregna-1,4-diene-3,20-dione. If, for example, there is a 17-propionyloxy substituent, the compound will be referred to as the 17-propionate or as 4-chloro-6α,9α-difluoro-11β-hydroxy-16α-methyl-17α-propionyloxy-21-methoxypregna-1,4-diene-3,20-dione.

If, however, in the compound of Formula (I), $X^1$ and $X^3$ are both chloro, $X^4$ is

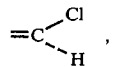

$X^2$ is fluoro, $R^1$ is hydrogen, $R^2$ is chloro, $R^3$ and $R^4$ together are isopropylidenedioxy, and there is a double bond between C-1 and C-2, the compound is 4,9α,11β,21-tetrachloro-6α-fluoro-16α,17α-isopropylidenedioxypregna-1,4-diene-3,20-dione.

ADMINISTRATION AND FORMULATION

The compounds of this invention are useful for the relief of inflamed conditions in mammals, and more specifically are useful for relieving inflammatory manifestations of corticosteroid responsive dermatoses in humans. Initial approximation of anti-inflammatory activity is done by following the procedure of McKenzie, S. W. and Stoughton, R. B., "Method for Comparing Percutaneous Absorption of Steroids" Arch Dermat, 86, 608 (1962) or modifications thereof.

Generally, the inflammatory manifestation in mammals, particularly humans, is combatted by treating the afflicted mammal with a therapeutically effective amount of at least one of the novel steroids of this invention, that is an amount which results in improvement of the inflamed condition. Preferably the steroids are first formulated to prepare a suitable pharmaceutical formulation, as discussed hereinafter, which is then placed in contact with the afflicted area. A therapeutically effective amount will depend upon the particular condition and the mammal receiving the treatment but will vary between 0.001% to 10% by weight of the pharmaceutical composition and preferably will be between 0.01 and 1% by weight of the formulation. Using these levels in the formulation, a therapeutically effective, non-side effect producing amount, i.e. enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the mammal's system.

The novel steroids of this invention may be formulated with suitable pharmaceutical excipients known in the art to form particularly effective anti-inflammatory compositions. Generally an effective amount of the steroid is about 0.001%w to about 10%w of the total formulated composition. The rest of the formulated composition will be about 90%w to about 99.999%w of suitable excipients which may include a pharmaceutically acceptable solvent and other pharmaceutically acceptable additives to form an effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and a glycol such as 1,2-propylene diol (i.e. propylene glycol), 1,3-propylene diol, polyethylene glycol having a molecular weight of from 100 to 10,000, dipropylene glycol, etc.; and mixtures of the aforementioned with each other.

A topical cream may be prepared as a semi-solid emulsion of oil in water or water in oil. A cream base formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in the following table:

| | |
|---|---|
| Water/glycol mixture (15% or more glycol) | 50-99 parts by weight |
| Fatty alcohol | 1-20 |
| Non-ionic Surfactant | 0-10 |
| Mineral oil | 0-10 |
| Typical pharmaceutical adjuvants | 0-5 |
| Active Ingredients | 0.001-10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White petrolatum | 40-94 pars by weight |
| Mineral Oil | 5-20 |
| Glycol solvent | 1-15 |
| Surfactant | 0-10 |
| Stabilizer | 0-10 |
| Active Ingredients | 0.001-10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | |
|---|---|
| Active Ingredients | 0.001-10.0 parts by weight |
| Propylene Carbonate | 1-10 |
| Solvent | 1-10 |
| Surfactant | 1-10 |
| White Petrolatum | 70-97 |

Suitable solvents, surfactants, stabilizers, etc. are discussed in U.S. Pat. No. 3,934,013 and such discussion is incorporated herein by reference.

A suitable "non-classical" anhydrous, water washable "ointment type" base is described in U.S. Pat. No. 3,952,930 to Katz and Neiman, and that patent is incorporated herein by reference. A representative composition of this invention utilizing such a base is is follows:

| | |
|---|---|
| Glycol solvent | 40-35 parts by weight |
| Fatty alcohol | 15-45 |
| Compatible plasticizer | 0-15 |
| Compatible coupling Agent | 0-15 |
| Penetrant | 0-20 |
| Active Ingredients | 0.001-10.0 |

PROCESS FOR PREPARING THE COMPOUNDS OF THE INVENTION

The novel compounds of this invention are ultimately obtained by converting a compound represented by Formula (IV) to the corresponding compound of this invention represented by Formula (I) wherein $X^1$, $X^2$, $X^3$, $X^4$, $R^1$, $R^2$, $R^3$ and $R^4$ are defined hereinbefore.

An overall process for preparing the pregna-1,4-dienes compounds of the invention is a three step process which is illustrated by the following Reaction Sequence 1, wherein $X^3$ is chloro, fluoro or bromo and the other substituents are defined hereinbefore for the broadest aspect of the invention.

REACTION SEQUENCE 1

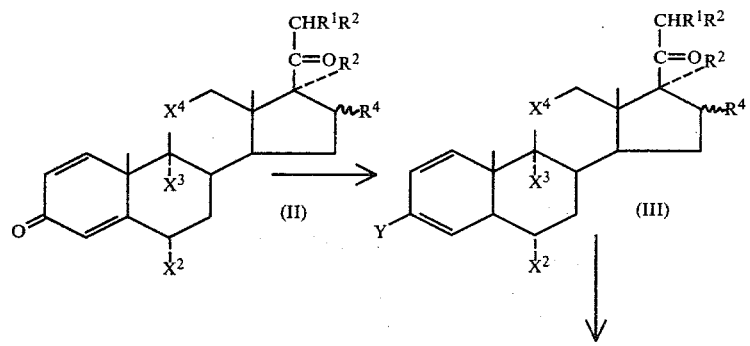

REACTION SEQUENCE 1

-continued

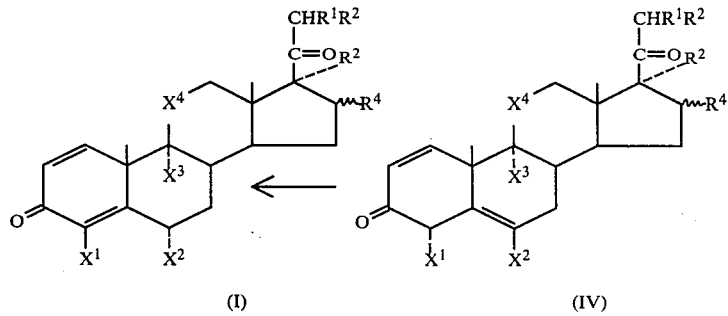

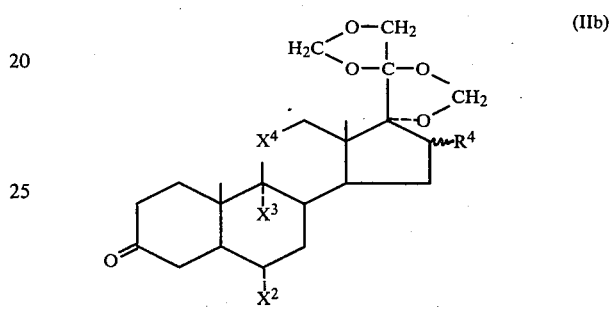

In the first step a compound represented by formula (II) is reacted to form a compound of the formula (III) wherein Y is methoxy or ethoxy. If, in the starting compound represented by formula (II), $R^2$ is hydroxy and $R^1$ is hydrogen then $R^2$ should be protected by acetylation or some similar means. If there is a β-hydroxy at the 11 position it is preferable that this hydroxy is also protected by acetylation or the like. Protection of both positions is readily accomplished by reacting the compound represented by (II) with acetic anhydride in pyridine and triethylamine in the presence of catalytic amounts of dimethyl amino pyridine at about 10° to about 100° C., preferably at room temperature, to give a compound of formula (IIa)

where $R^5$ and $R^6$ are each

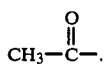

Although such protection is not needed in the case of the 11β-hydroxy, it does improve the yield.

If compound (II) is a 17α,21-dihydroxypregna-1,4-diene where $R^4$ is methyl or hydrogen, it is preferably reacted with acid aqueous formaldehyde to form the 17α,21:20,21-bis methylenedioxy compound of the formula Thus both the 17 and 21 hydroxy moieties are protected from reaction. Once the hydroxy groups, if any, are protected, compound (II), (IIa) or (IIb) is reacted with, for example, a large excess of trimethyl orthoformate in methanol or triethyl orthoformate in ethanol in the presence of a catalytic amount of a suitable acid catalyst, such as fuming sulfuric acid, at reflux temperature or less. About 50°–55° C. is preferred. Generally the molar ratio of trimethyl orthoformate or triethyl orthoformate to the compound represented by formula (II), (IIa) or (IIb) is about 10:1 to about 30:1, preferably about 10:1 to 15:1. Once the reaction is complete a base is added to neutralize the acid and the resulting enol-ether represented by formula (III) or the enol-ether corresponding to the compound represented by formulas (IIa) or (IIb) where Y is methoxy or ethoxy is recovered and purified using methods well known in the art such as evaporation, recrystallization, etc.

The enol-ether is then fluorinated or chlorinated using perchloryl fluoride ($ClO_3F$) or trifluoromethoxy fluoride ($CF_3OF$) as a fluorinating agent, a source of positive chlorine such as N-chlorosuccinimide, dichlorohydantoin, etc. as a chlorinating agent, to form the 3-keto-4α-fluoro(chloro)pregna-1,5-diene represented by formula (IV) or the 3-keto-4α-fluoro(chloro)-pregna-1,5-diene corresponding to the compound represented by formulas (IIa) or (IIb).

In the case of $ClO_3F$, which is a gas, an approximately equimolar amount (1 to 1.1 moles $ClO_3F$ per mole of the enol-ether) is metered in to a mixture of the enol-ether in a solution which is a major amount of acetone, preferably 90% by weight, and a minor amount of water, preferably about 10% over a period of about 1–3 hours at 10°–30° C., preferably ambient temperature. Dichlorohydantoin is similarly reacted.

The compound of formula (IV) or the corresponding compound of formulas (IIa) or (IIb), in turn, is reacted either with KF in sulfolane at 60°–70° C. or in an inert atmosphere, e.g. nitrogen, with a suitable base such as an alkali metal carbonate, e.g. potassium carbonate, in a suitable oxygenated hydrocarbon solvent such as an alkanol, e.g. methanol, to cause a rearrangement to take place to form the desired 4-fluoro (4-chloro)-3-keto pregna-1,4-diene.

If appropriate, the protecting groups at the 11β,17α- and/or 21-positions are hydrolyzed using a suitable base such as 1 molar sodium hydroxide if the treatment with, e.g. potassium carbonate is not sufficient. Where $X^3$ is fluoro, chloro or bromo, potassium carbonate is generally sufficient for hydrolysis of the 11β-acetoxy group. In the case of the 9α-chloro- or 9α-bromo-11β-hydroxy compound, the treatment with potassium carbonate or sodium hydroxide may form a 9,11-epoxide. This can be converted to the 9,11-chlorohydrin or 9,11-bromohydrin compound by reacting the 9,11-epoxide with hydrochloric or hydrobromic acid in chloroform respectively. The BMD compound is hydrolyzed using a suitable acid such as 60% formic acid or 48% hydrofluoric acid.

Once the final pregna-1,4-diene is obtained, the compound may be readily selectively hydrogenated across the 1-2 bond by any suitable means known in the art to obtain the corresponding $\Delta^4$-3-keto steroid.

Compounds of this invention represented by Formula (I) wherein $X^1$, $X^2$, $X^3$ and $X^4$ are as defined in the broadest aspect of this invention $R^1$ is hydrogen, $R^2$ is hydroxy or alkanoyloxy, $R^3$ is alkanoyloxy and $R^4$ is α-methyl or β-methyl are prepared by (1) reactively contacting the 17α,21-dihydroxy compound with a suitable trialkyl orthoalkanoate to form the 17α,21-orthoester; (2) hydrolyzing the thus formed 17α,21-orthoester to form the 21-hydroxy-17α-ester; and (3) if a 21-alkanoyloxy compound reactively contacting the 17α-ester with a suitable anhydride or acid chloride to form the desired 17,21-diester (symmetrical or un symmetrical).

(1) The first step in the process for preparing the 17α,21-orthoesters of this invention is performed by mixing a substantial molar excess of the trialkyl orthoester, with the 17α,21-dihydroxy compound in the presence of a catalytic amount of a suitable acid. The reaction can be carried out neat or in the presence of a suitable solvent. If neat, the excess orthoester acts as a diluting agent to aid in reaction and a molar excess of at least 10 moles of the orthoester per mole of the 17α,21-dihydroxy compound is used, preferably the molar ratio is about 30-40:1. If a solvent is employed, a molar excess of less than 10 moles of the orthoester per mole of the 17α,21-dihydroxy compound is required. The trialkyl orthoesters which are used include, for example, trimethyl orthoacetate, trimethyl orthopropionate, trimethyl orthobutyrate, trimethyl orthovalerate, trimethyl orthohexanoate, and the like.

Suitable solvents which can be used include inert organic solvents such as benzene, toluene, and the like. Suitable acid catalysts include p-toluenesulfonic acid (pTSA), sulfuric acid, perchloric acid, methanesulfonic acid, and the like. The reaction takes place at temperatures of about 50° C. to about 150° C., preferably at about 110° C. to 120° C. neat or at the boiling point of the orthoester solvent, whichever is lower. Generally, the reaction goes to completion in less than 5 hours, 1-2 hours being sufficient for the neat reaction at 110°-120° C. Once the reaction is completed, the 17α,21-orthoester is isolated and purified by using well established means such as extraction, separation, solvent evaporation, recrystallization and thin-layer chromatography (TLC).

(2) Once the 17α,21-orthoester is obtained it is contacted with a buffered aqueous alcohol solution to hydrolyze the 17α,21-orthoester and form the 17α-ester. A suitable buffering agent is potassium hydrogen phosphate buffer having a pH of 3-3.5. Suitable alcohols include methanol, ethanol, propanol and the like. A mixture of 5-10 parts by volume of the alcohol solvent per part of the aqueous buffer has been found to be suitable. The reaction takes place at temperatures of 20° C. to 50° C. At about 25° C. the reaction is complete in 24 hours or less. The 17α-ester is then purified by methods well-known in the art, e.g. extraction, solvent evaporation, crystallization, TLC, etc.

(3) To obtain the 17α,21-diesters (symmetrical or unsymmetrical), the 21-hydroxy 17α-ester compound is reacted with a suitable acid chloride or acide anhydride in a solvent in the presence of an organic base. Bases which may be used include pyridine, 4-dimethylaminopyridine, triethylamine, and the like, while suitable solvents are chloroform, methylene chloride, benzene and the like. In a preferred procedure, pyridine is used both as the base and the solvent. The acid chloride and anhydride is present in a substantial molar excess such as 5-20 moles of the acid chloride per mole of 17α-ester. Enough base is used to neutralize the acid formed by the reaction, thus at least one mole of base is needed per mole of 17α-ester. Suitable acid chlorides include, for example, acetyl chloride, propionyl chloride, butyryl chloride, valeroyl chloride or hexanoyl chloride while useful anhydrides include, for example, acetic anhydride, proprionic anhydride, butyric anhydride, valeryl anhydride and hexanoyl anhydride. Generally, the reaction takes place readily at temperatures of 0°-50° C., preferably at about 20° C.-30° C.

To prepare the 4-halopregn-4-enes of formula (I) of this invention wherein $X^3$ is hydrogen, a slightly modified route is used as set forth in Reaction Sequence 2:

REACTION SEQUENCE 2

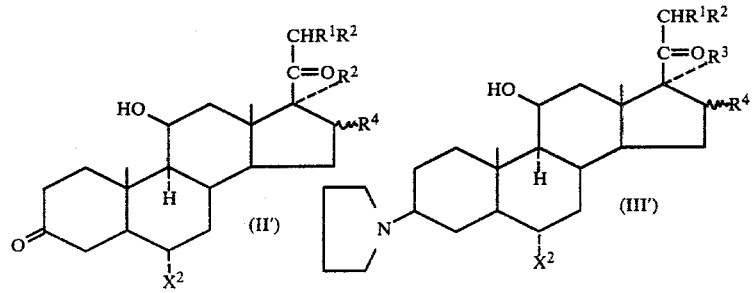

REACTION SEQUENCE 2

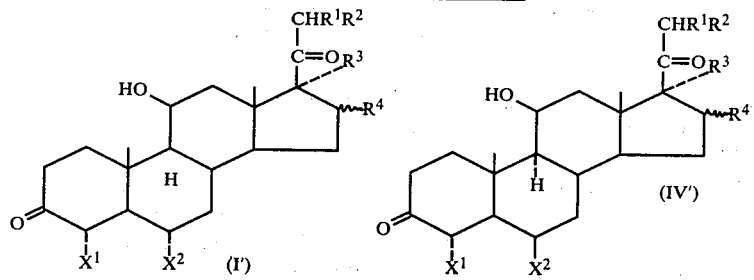

In this sequence, the starting 3-keto-pregn-4-ene represented by formula (II') is first reacted with a suitable amine such as pyrrolidine to form the enamine represented by Formula (III'). Generally this reaction takes place readily in a suitable inert organic solvent such as benzene or methanol.

The enamine represented by formula (III') is then fluorinated for chlorinated according to the procedure set forth above to form the 4α-fluoro (chloro)-3-keto-pregn-5-ene of formula (IV') which in turn is treated with, e.g. potassium carbonate in methanol under $N_2$, to shift the double bond to the 4-position (if the double bond has not already shifted) thus giving a compound of this invention represented by (I'). The resulting 3-keto-pregn-4-ene is readily dehydrogenated at the 1-position by methods known in the art such as using 2,3-dichloro-4,6-dicyano-1,4-benzoquinone in dioxane. Any protecting groups at 11β-, 17α-, or 21 are readily hydrolyzed by methods discussed hereinbefore.

Alternatively, 16α-methyl or 16β-methyl compounds of this invention are prepared according to Reaction Sequence 3.

REACTION SEQUENCE 3

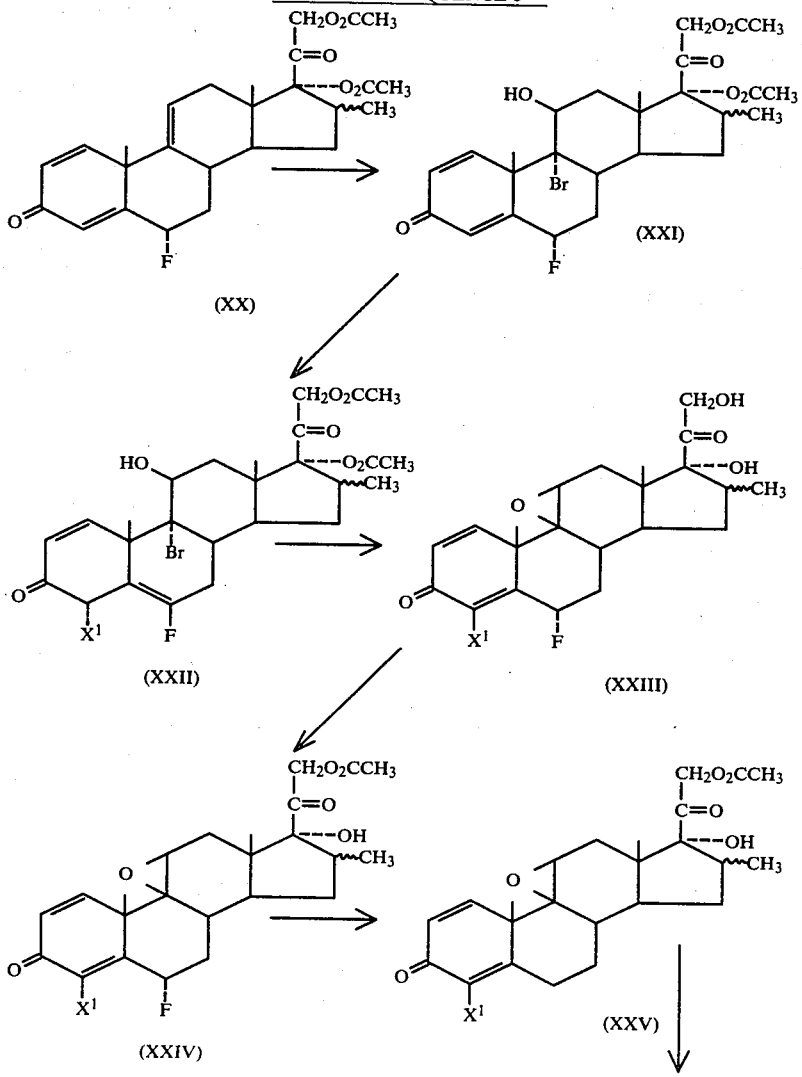

-continued
REACTION SEQUENCE 3

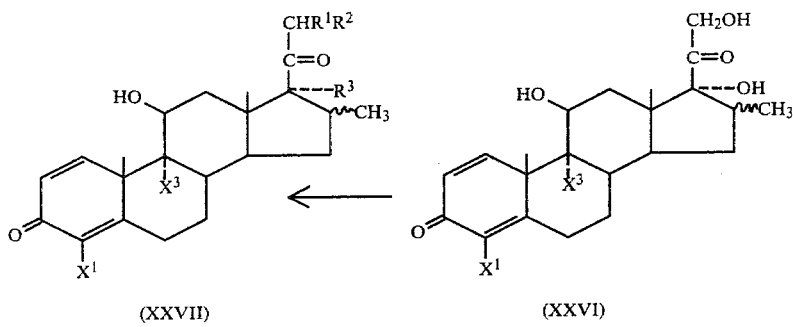

(XXVII)         (XXVI)

The starting compound in this sequence is shown as Formula (XX). This is a known compound, e.g. see British Pat. No. 1,403,962. The starting material is converted into the 9,11-bromohydrin of Formula (XXI) by treating with dibromohydantoin according to methods well known in the art. This compound is readily converted to the 4-fluoro or 4-chloro compound of Formula (XXII) by treatment with trialkyl orthoformate and then with perchlorofluoride or N-chlorosuccinimide as discussed hereinbefore. The resulting compound represented by Formula (XXII) is converted to a compound of Formula (XXIII) by treatment with a base such as potassium carbonate and anhydrous methanol in an inert atmosphere to form the corresponding epoxide having a hydroxy at the 17α and 21 positions. This in turn is converted to the 21 acetate of Formula (XXIV) by reaction with acetic anhydride in pyridine.

This compound, in turn, is treated with zinc metal dust and 3% cupric acetate and acetic acid in anhydrous methanol and methylene chloride at ambient temperatures to give a 6-desfluoro compound of Formula (XXV).

By treatment with basic methanol in an inert atmosphere, this compound is hydrolyzed to the 17α,21-dihydroxy compound (not shown), which in turn is then be converted to the corresponding fluorohydrin, chlorohydrin or bromohydrin by methods known in the art such as using hydrofluoric acid, hydrochloric acid or hydrobromic acid, respectively to give a compound of Formula (XXVI) wherein $X^1$ is fluoro or chloro and $X^3$ is fluoro, chloro or bromo. This then is elaborated using methods known in the art to give compounds of this invention represented by Formula (XXVII).

For example, the 21-chloro, bromo or fluoro group is introduced by treating a 21-hydroxy steroid derivative with methanesulfonyl chloride in pyridine, then refluxing the resulting 21-mesylate ester with lithium chloride or lithium bromide in sulfolane from ambient temperatures to about 135° C. to get the corresponding 21-chloro or -bromo steroid derivative. The 21-fluoro steroid is obtained by refluxing the 21-bromide with potassium fluoride in sulfolane from ambient temperatures to about 135° C. Preferably the 21-bromo compound is isolated before preparing the 21-fluoro compound. Further discussion of the preparation of these 21-halosteroids can be found in U.S. Pat. No. 3,053,838 to Fried.

The 21-acyloxy compounds are readily prepared by reacting the known corresponding 21-hydroxy compounds, e.g. prednisolone, with the desired alkanoyl chloride or, preferably, anhydride and an organic base, e.g. pyridine.

The 21,21-dihalo steroids are readily prepared according to the processes disclosed in U.S. Pat. No. 4,065,452 issued Dec. 27, 1977. Formylating an appropriate 16αpregna-1,4,9(11)-triene-3,20-dione with ethyl formate in a hindered base to form a hydroxy-methylene group at 21; halogenating at 21 with, e.g., lithium chloride, cupric bromide, or perchloryl fluoride to form a 21,21-dihalo-21-formyl; and deformylating with sodium hydroxide to form the 21,21-dihalo steroid.

To prepare the 21,21-dihydroxy and 21,21-dialkoxy steroids, the process set forth in U.S. Pat. No. 4,011,315 is particularly useful and that patent is incorporated herein by reference. In this process, an appropriate 21-hydroxy steroid is contacted with air in the presence of a copper (II) catalyst such as cupric acetate to yield the 21,21-dihydroxy steroid (i.e. a 21-aldehyde hydrate). The reaction is preferably conducted in methanol at a temperature of 50° to 80° C. for a period of 30 minutes to 60 hours.

The 21-aldehyde hydrate can then be isolated according to methods known in the art or may then be heated under vacuum at a temperature of 100° C. for a period of 30 minutes to 3 hours to yield the 21-aldehyde which is reacted with a lower alkanol containing 1 to 8 carbon atoms, preferably methanol, at a temperature of 20° to 60° C. for a period of 15 minutes to 1 hour to yield a 21-aldehyde hemiacetal.

Reaction of the 21-aldehyde hemiacetal with a suitable halogenating agent such as methane sulfonyl chloride, thionyl chloride, or thionyl bromide in the presence of an organic base such as triethylamine, pyridine and the like yields the 21-halo-21-alkyl ether. The reaction is preferably conducted in a chlorinated organic solvent such as methylene chloride, chloroform, 1,1-dichloroethane and the like for a period of 1 to 16 hours and a temperature of $-20°$ to $+10°$ C. The thus obtained 21-halo-21-alkyl ether is then treated with an alkali metal alkoxide, preferably a sodium alkoxide such as sodium methoxide. The reaction is conducted in a solvent medium usually containing the alkanol corresponding to the alkoxide utilized although a solvent inert to the other reactants may be employed. Reaction temperatures are preferably maintained at 20° to 60° C. for a period of 2 to 6 hours.

Another procedure for preparing compounds of this invention is set forth in Reaction Sequence 4, below.

REACTION SEQUENCE 4

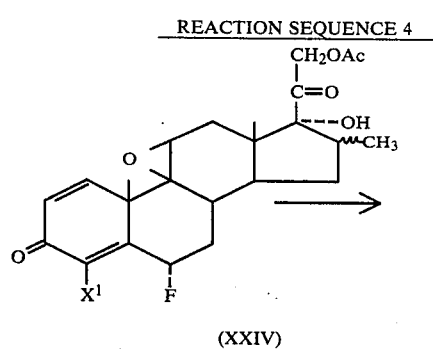

(XXIV)

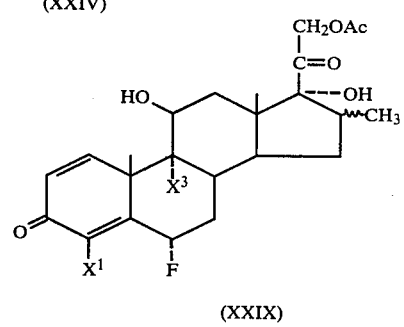

(XXIX)

-continued
REACTION SEQUENCE 4

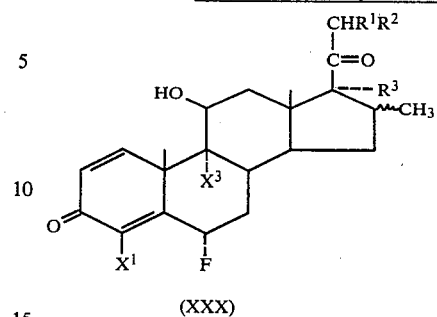

(XXX)

In this process the intermediate compound represented by Formula (XXIV) prepared as discussed above for Reaction Sequence (3) is reacted with HF in tetrahydrofuran and chloroform at very low temperatures ($-70°$ C.) or with a HF/urea complex according to the process of U.S. Pat. No. 3,211,758 to Tarkoey. This forms a compound represented by Formula (XXIX) (where $X^3$ is fluoro) which is elaborated to other compounds of this invention by methods discussed hereinbefore.

Another process for preparing 9α-chloro compounds of this invention is set forth in Reaction Sequence 5, below.

REACTION SEQUENCE 5

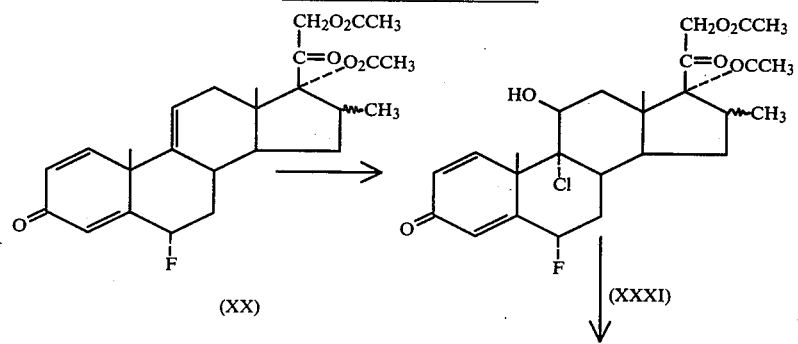

(XX)    (XXXI)

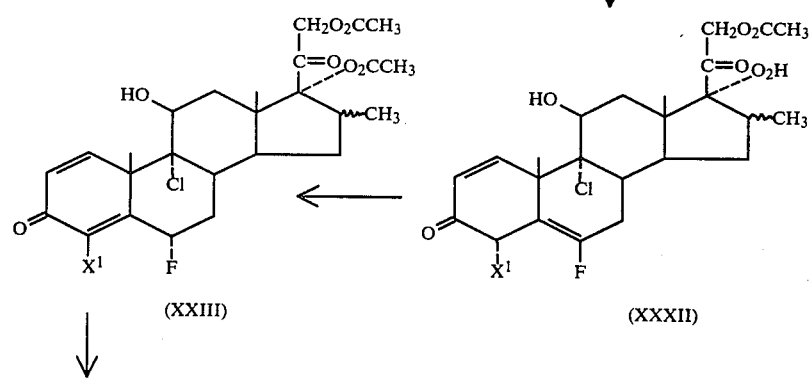

(XXIII)    (XXXII)

REACTION SEQUENCE 5

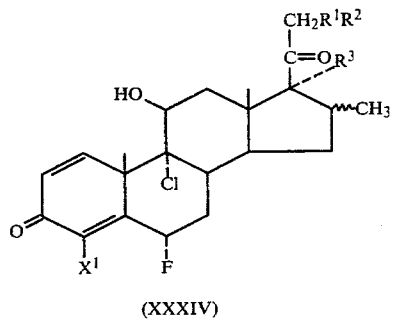

(XXXIV)

In the first step of Reaction Sequence 5, the 1,4,9(11)-triene is reacted with Halane (1,3-dichloro-5,5-dimethylhydantoin) to form the 9,11-chlorohydrin of Formula (XXXI). This, in turn, is fluourinated or chlorinated at the 4-position using procedures set forth hereinbefore to give a compound of this invention represented by Formula (XXXIII) which is readily elaborated to other compounds of this invention represented by Formula (XXXIV) wherein $X^1$, $R^1$, $R^2$ and $R^3$ are defined above.

Methods of preparing 9α-unsubstituted compounds of this invention are set forth in Reaction Sequence 6, below.

REACTION SEQUENCE 6

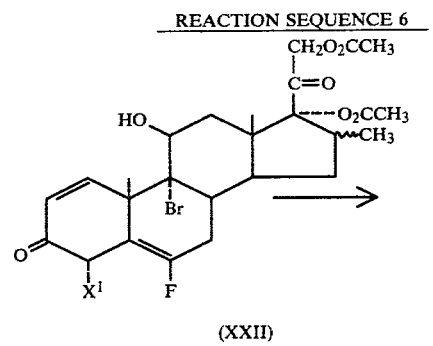

(XXII)

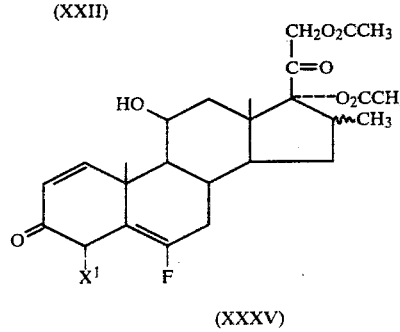

(XXXV)

-continued
REACTION SEQUENCE 6

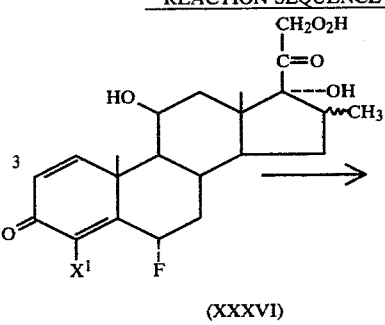

(XXXVI)

(XXXVII)

In this process, the starting compound of Formula (XXII) (prepared as discussed in Reaction Sequence 3) is treated with a molar excess (preferably 10–15 times) of tributyl tin hydride in tetrahydrofuran at reflux temperature until the reaction is complete, generally about 2–3 hours. This results in a compound having a hydrogen at the 9α-position represented by Formula (XXXV). This in turn is converted to a compound of Formula (XXXVI) by treatment with potassium carbonate in methanol in an inert atmosphere as discussed hereinbefore. This is then elaborated to other compounds of this invention represented by Formula (XXXVII), where $X^1$, $R^1$, $R^2$ and $R^3$ are defined above, using methods discussed hereinbefore.

In Reaction Sequence 7, below, compounds of this invention are prepared which are unsubstituted at both the 6α and 9α positions.

REACTION SEQUENCE 7

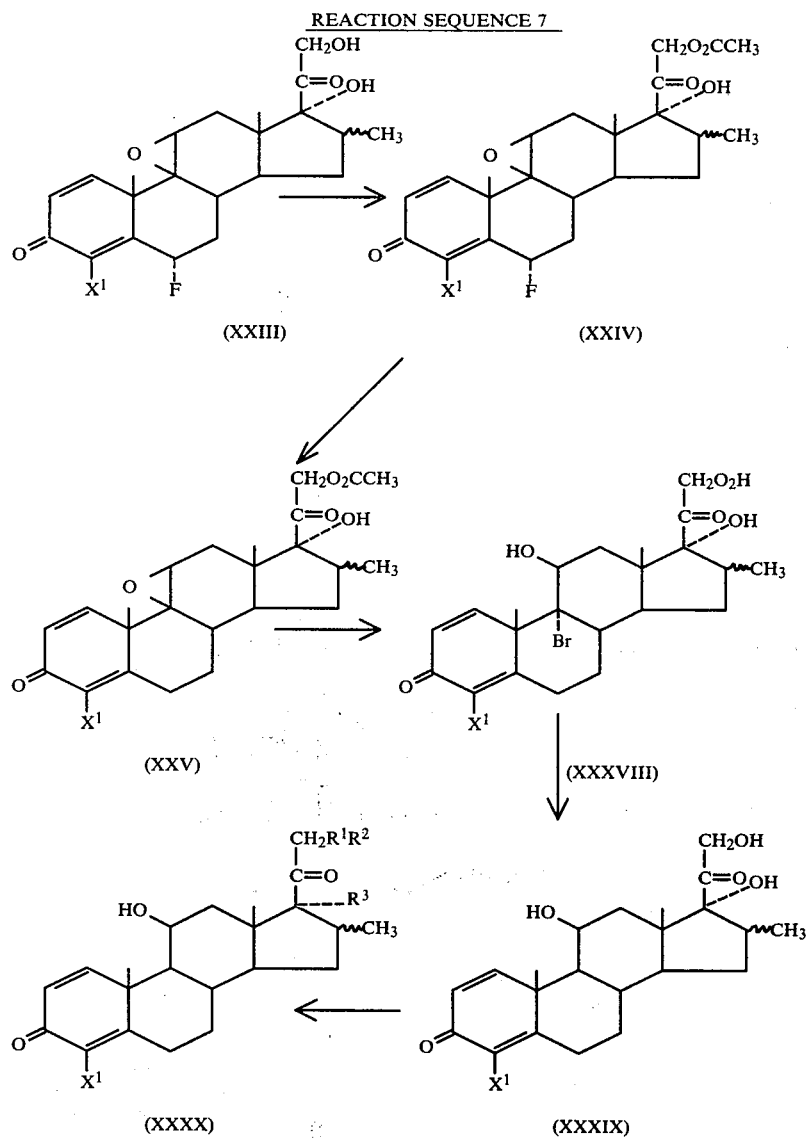

The compound represented by Formula (XXV) is prepared as in Reaction Sequence 3. The 9,11-bromohydrin of Formula (XXXVIII) is prepared using HBr according to methods known in the art and then is converted to the 9-desbromo compound of Formula (XXXIX) using tributyl tin hydride as discussed hereinabove. That compound is then converted to the compounds of this invention represented by Formula (XXXX) wherein $X^1$, $R^1$, $R^2$ and $R^3$ are defined hereinbefore.

More specific embodiments of the process of this invention are given hereafter in the Examples.

PREPARATION OF STARTING COMPOUNDS AND GENERAL PROCEDURES

The following discussion sets forth procedures for preparing starting materials as well as procedures for modifying compounds of this invention.

As pointed out above, starting compounds for the process of preparing the compounds of this invention by Reaction Sequence 1 or 2 are represented by the Formulas (II) or (II') wherein the substituents are described hereinbefore for each of the respective formulas and are either known per se or are readily prepared using known techniques. For example, pregna-1,4,9(11)-trienes are treated with chlorine according to the process of U.S. Pat. No. 3,009,933 to give the corresponding 9α,11β-dichloropregna-1,4-diene. The 9α-bromo-11β-hydroxy or 9α-chloro-11β-hydroxy compounds are prepared by reacting the appropriate pregna-1,4,9(11)-triene with dibromohydantoin or N,N'-dichloro-dimethylhydantoin to form the 9α,11β-bromohydrin or 9α,11β-chlorohydrin, respectively. The 9α,11β-bromohydrin steroid is in turn reacted with sodium hydroxide to give the corresponding 9β,11β-epoxide which is then treated with a hydrogen fluoride/urea complex according to the process set forth in U.S. Pat. No. 3,211,758 to Tarkoey to give the 9α-fluoro-11β-hydroxy compound.

An 11β-hydroxy (9α-unsubstituted) steroid is readily prepared from a 3-keto-6α-optionally substituted-pregna-1,4-diene or pregn-4-ene by methods well known in the art such as employing *Cunninghamella blakesleeana, Cunninghamella bainieri, Curvularia Lunata,* or other suitable micro-organisms in ethanol which selectively affords the desired 11β-hydroxy steroid.

16α,17α-Isopropylidenedioxy-pregna-1,4,9(11)-trienes are known or can readily be prepared by reacting an 11β-hydroxy-16α,17α-isopropylidenedioxypregna-1,4-diene with thionyl chloride in pyridine at 0° C. A 17α-hydroxypregna-1,4-9(11)-triene is prepared by reacting the corresponding 11β,17α-dihydroxy-pregna-1,4-diene with methane sulfonyl chloride in pyridine with SO₃ at about 0° C. or with methyl chlorosulfinate (prepared by distilling methanol with thionylchloride) in tetrahydrofuran and pyridine at −78° C. and allowing the reaction mixture to slowly warm to ambient temperature.

A 16α,17α-isopropylidenedioxy group is readily introduced by treating the corresponding 16α,17α-dihydroxy steroid with acetone in the presence of perchloric acid. The 16α,17α-dihydroxy groups are introduced by treating a pregn-16-ene derivative with potassium permanganate, acetone and acetic acid.

A 16-methyl group is introduced by treating the corresponding 20-keto-pregn-16-ene steroid with methyl magnesium bromide in the presence of cuprous chloride in an ether such as tetrahydrofuran. The 20-keto-pregn-16-ene steroid is prepared by preparing the 3,20-bissemicarbazone of a 3,20-diketo-17α-hydroxy steroid, treating it with glacial acetic acid and acetic anhydride and then allowing the resulting product to react with aqueous pyruvic acid.

The 17α-hydroxy group is introduced in conjunction with the 16-methyl group by first treating the corresponding 16-methyl-pregn-16-ene steroid (which is prepared by treating the corresponding pregn-16-ene steroid with diazomethane and then heating the resulting product to 180° C.) with hydrogen peroxide, in an aqueous basic media, then permitting the resulting 16,17-oxido-16-methyl steroid to react with hydrogen bromide in glacial acetic acid. The resulting olefin is hydrogenated with the use of a palladium catalyst to afford the corresponding 16α-methyl-17α-hydroxy derivative.

By following the procedures set forth above for preparing the starting material for the compounds of this invention, steroids of a relatively simple structure can be converted to other structures as desired. Thus, exemplary known compounds which can be employed to prepare starting materials for compounds of this invention according to procedures discussed above include progesterone, corticosterone, hydrocortisone, prednisolone, betamethasone, dexamethasone, triamcinolone, paramethasone, fluocinolone, triamcinolone acetonide, fluocinolone acetonide, and the like.

Further specific embodiments of this invention are found in the following examples which are given by way of illustration only and are not to be interpreted as limiting the scope of the claims appended hereto.

EXAMPLE I

This example sets forth a process for preparing 4,6α,9α-trifluoro-11β-hydroxy-16α,17α-isopropylidenedioxypregna-1,4-diene-3,20-diones (which are substituted at the 21 position) according to the following reaction sequence:

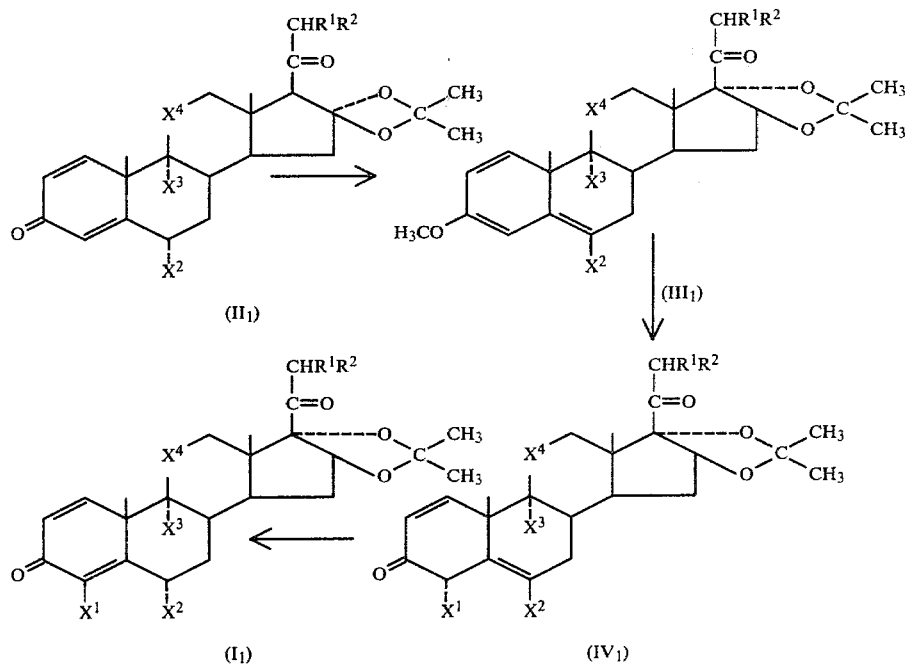

A. Preparation of 4,6α,9α-trifluoro-11β,21-dihydroxy-16α,17α-isopropylidenedioxypregna-1,4-diene-3,20-dione.

Ten grams (g) fluocinolone acetonide (6α,9α-difluoro-11β,21-dihydroxy-16α,17α-isopropylidenedioxypregna-1,4-diene-3,20-dione) is stirred into 30 milliliters (ml) of acetic anhydride, 30 ml triethylamine and 1 g 4-N,N-dimethylamino pyridine at room temperature for 5 hours to form the corresponding 11β,21-diacetate ($X^2$ and $X^3$ are F, X is

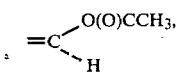

$R^2$ is acetoxy and $R^1$ is H) which is then recovered by precipitation in water and filtration.

To a solution of 620 ml trimethyl orthoformate, 206 ml anhydrous methanol, and 4.1 ml fuming sulfuric acid, 42 g of the 11β,21-diacetate of fluocinolone acetonide prepared according to the preceeding paragraph is added. The resulting mixture is stirred at 50°–55° C. for 30 minutes, at which time thin layer chromatography (TLC) using an eluant of 35% ethyl acetate and 65% hexane shows that the reaction is complete. Twenty-five ml of triethyl amine are added to neutralize the acid and the solvents are removed using a rotary evaporator at reduced pressure. The residue is dissolved in 500 ml of acetone, about 25 ml water is added and the acetone is removed under reduced pressure to give crystalline precipitate which is collected by filtration and air dried overnight to give 40 g. of compound (III$_1$), above, wherein R$^1$ is hydrogen, R$^2$ is acetoxy, R$^4$ is

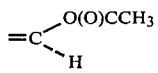

and X$^2$ and X$^3$ are F.

Thirty g of the resulting product is added to 300 ml of a solvent consisting of 90% by weight (%w) acetone and 10 %w water and molar equivalent of perchloryl fluoride (ClO$_3$F) is added at ambient temperature over about 30 minutes. TLC of the reaction mixture using a mixture of 35% ethyl acetate and 65% hexane shows the reaction to be complete upon completion of the ClO$_3$F addition. Water is slowly added to the reaction mixture until a total volume of 2 l is obtained. A crystalline precipitate forms which is collected by filtration, dissolved in 300 ml methylene chloride (CH$_2$Cl$_2$) and the resulting solution is dried over anhydrous sodium sulfate. The product represented by (IV$_1$) (wherein R$^1$ is hydrogen; R$^2$ is acetoxy; X$^1$, X$^2$ and X$^3$ are F; and X$^4$ is

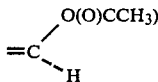

is purified by chromatography on 300 g column of silica gel, eluting with a mixture of 75% CH$_2$Cl$_2$ and 25% hexane. The homogeneous fractions are combined, concentrated to dryness, and the residue is crystallized from CH$_2$Cl$_2$/CH$_3$OH to give 15 g of a compound represented by formula (IV$_1$) wherein R$^1$ is hydrogen, R$^2$ is acetoxy and X$^4$ is

One g of the resulting product is stirred with 20 ml methanol and 20 ml CH$_2$Cl$_2$ containing 200 milligrams (mg) of anhydrous potassium carbonate under nitrogen at atmospheric pressure and ambient temperature for one hour, at which time TLC shows the reaction is complete. The reaction mixture is diluted with 20 ml methanol and 2 ml glacial acetic acid and concentrated under reduced pressure to a small volume. The crystalline precipitate which forms is collected by filtration and washed with methanol and water to give 800 mg of the final product, namely 4,6α,9α-trifluoro-11β,21-dihydroxy-16α,17α-isopropylidenedioxypregna-1,4-diene-3,20-dione, melting point (mp) 270°–271.5° C., $_D[\alpha]$ 108° (CHCl$_3$).

B. Ten g of the final product from step A are cooled with 10 ml mesyl chloride in 100 ml pyridine at 0° C. for 1 hour and the resulting mixture is poured into water to form a precipitate which is filtered and air dried to give the 21-mesylate corresponding to formula (I$_1$), wherein R$^1$ is H, R$^2$ is a mesyl ester and X$^4$ is

Ten g of this material is reacted with lithium chloride in 100 ml sulfolane at 100° C. for 8 hours. Water is added to form a precipitate which is collected by filtration, air dried and recrystallized from CH$_2$Cl$_3$-MEOH to give 4,6α,9α-trifluoro-11β-hydroxy-16α,17α-isopropylidenedioxy-21-chloropregna-1,4-diene-3,20-dione, m.p. 285.5°–289.0° C., [α]$_D$(Pyridine).

C. By following the procedure set forth in part A of this example but substituting the appropriate starting material for fluocinolone acetonide the following compounds are prepared:

4,6α,9α,21-tetrafluoro-11β-hydroxy-16α,17α-isopropylidenedioxypregna-1,4-diene-3,20-dione, m.p. 280°–281° C.;

4,6α,9α,21,21-pentafluoro-11β-hydroxy-16α,17α-isopropylidenedioxypregna-1,4-diene-3,20-dione;

4,6α,9α-trifluoro-11β-hydroxy-16α,17α-isopropylidenedioxy-21,21-dichloropregna-1,4-diene-3,20-dione;

4,6α,9α-trifluoro-11β-hydroxy-16α,17α-isopropylidenedioxy-21,21-dimethoxypregna-1,4-diene-3,20-dione, m.p. 268°–270° C., [α]$_D$ 30° (CHCl$_3$);

4,6α,9α-trifluoro-11β,21-dihydroxy-16α,17α-isopropylidenedioxypregna-1,4-diene-3,20-dione;

4,6α,9α-trifluoro-11β-hydroxy-16α,17α-isopropylidenedioxy-21-acetoxypregna-1,4-diene-3,20-dione;

4,6α,9α-trifluoro-11β-hydroxy-16α,17α-isopropylidenedioxy-21-propionyloxypregna-1,4-diene-3,20-dione and the like.

EXAMPLE 2

This example sets forth a process for preparing 4,6α-difluoro-9α,11β-dichloro-16α,17α-isopropylidenedioxypregna-1,4-diene-3,20-diones (which are substituted at the 21 position) according to the reaction of Example wherein X$^1$ and X$^2$ are both fluoro; X$^3$ and X$^4$ are both chloro; R$^1$ is hydrogen, fluoro, chloro, hydroxy or methoxy; and R$^2$ is fluoro, chloro, hydroxy or alkanoyloxy of 2 through 6 carbon atoms when R$^1$ is hydrogen or R$^2$ is the same as R$^1$ when R$^1$ is fluoro, chloro, hydroxy or methoxy.

A. 4,6α,21-Trifluoro-9α,11β-dichloro-16α,17α-isopropylidenedioxypregna-1,4-diene,2,30-dione.

To a solution of 620 ml trimethyl orthoformate, 206 ml anhydrous methanol, and 4.1 ml fuming sulfuric acid, is added 40 g of 6α,21-difluoro-9α,11β-dichloro-16α,17α-isopropylidenedioxypregna-1,4-diene-3,20-dione. The resulting mixture is stirred at 50°–55° C. for 30 minutes, at which time thin layer chromatography (TLC) using an eluant of 35% ethyl acetate and 65% hexane shows that the reaction is complete. Twenty-five ml of triethylamine are added to neutralize the acid and the solvents are removed using a rotary evaporator at reduced pressure. The residue is dissolved in 500 ml of acetone, about 25 ml water is added and the acetone is removed under reduced pressure to give a crystalline precipitate which is collected by filtration and air dried over night to give 39 g of compound (III$_2$), above, wherein R$^1$ is hydrogen, R$^2$ is fluoro, X$^2$ is fluoro, X$^3$ is chloro and X$^4$ is

Thirty g of the resulting product are added to 300 ml of a solvent consisting of 90% acetone and 10% water and a molar equivalent of ClO$_3$F are added at ambient temperature over about 30 minutes. TLC of the reaction mixture using an eluant of 35%w ethylacetate and 65%w hexane shows the reaction to be complete upon completion of the ClO$_3$F addition. Water is slowly added to the reaction mixture until a total volume of two liters is obtained. The crystalline precipitate which forms is collected by filtration, dissolved in CH$_2$Cl$_2$ and the resulting solution is dried over anhydrous sodium sulfate. The product represented by Formula (IV$_2$) wherein R$^1$, R$^2$, X$^2$, X$^3$ and X$^4$ are as defined in this example and X$^1$ is fluoro is purified by chromatography on a 300 g silica gel column eluting with a mixture of 75% CH$_2$Cl$_2$ and 25% hexane. The homogeneous fractions are combined, concentrated to dryness, and the residue crystallized from CH$_2$Cl$_2$/CH$_3$OH to give 15 g of a compound represented by Formula (IV$_1$) wherein R$^1$, R$^2$, X$^1$, X$^2$, X$^3$ and X$^4$ are defined in this example.

One g of the resulting product is stirred with 20 ml methanol and 20 ml CH$_2$Cl$_2$ containing 200 mg of anhydrous potassium carbonate under nitrogen at atmospheric pressure and ambient temperature for one hour, at which time TLC show the reaction is complete. The reaction mixture is diluted with 20 ml methanol and 2 ml glacial acetic acid and concentrated under reduced pressure to a small volume. The crystalline precipitate which forms is collected by filtration and washed with methanol and water to give 0.0 g of 4,6α,21-trifluoro-9α,11β-dichloro-16α,17α-isopropylidenedioxypregna-1,4-diene-3,20-dione, m.p. [α]$_D$ 149° (CHCl$_3$).

B. By following in principle the procedure set forth in part A of this example and using an appropriate starting material as set forth in the "Preparation of Starting Compounds" part of the specification, the following compounds are prepared:

4,6α,21,21-tetrafluoro-9α,11β-dichloro-16α,17α-isopropylidenedioxypregna-1,4-diene-3,20-dione;

4,6α,21-trifluoro-9α,11β,21-trichloro-16α,17α-isopropylidenedioxypregna-1,4-diene-3,20-dione;

4,6α-difluoro-9α,11β,21,21-tetrachloro-16α,17α-isopropylidenedioxypregna-1,4-diene-3,20-dione;

4,6α-difluoro-9α,11β,21-trichloro-16α,17α-isopropylidenedioxypregna-1,4-diene-3,20-dione, mp 254.5°-256.5° C., [α]$_D$+164 (CHCl$_3$);

4,6α-difluoro-9α,11β-dichloro-16α,17α-isopropylidenedioxy-21,21-dimethoxypregna-1,4-diene-3,20-dione;

4,6α-difluoro-9α,11β-dichloro-16α,17α-isopropylidenedioxy-21-hydroxypregna-1,4-diene-3,20-dione;

4,6α-difluoro-9α,11β-dichloro-16α,17α-isopropylidenedioxy-21-valeryloxypregna-1,4-diene-3,20-dione;

4,6α-difluoro-9α,11β-dichloro-16α,17α-isopropylidenedioxy-21-acetoxy-1,4-dione-3,20-dione; and the like.

EXAMPLE 3

This example sets forth a process for preparing 4-chloro-6α,9α-difluoro-11β-hydroxy-16α,17α-isopropylidenedioxypregna-1,4-diene-3,20-diones (which are substituted at the 21 position similarly to Example 2) according to the reaction sequence of Example 1 wherein X$^1$ is chloro, X$^2$ and X$^3$ are both fluoro and X$^4$ is

A. By following in principle the procedure of Example 1, Part A but substituting 21-chloro-6α,9α-difluoro-11β-hydroxy-16α,17α-isopropylidenedioxypregna-1,4-diene-3,20-dione for fluocinolone acetonide and dichlorohydantoin for ClO$_3$F, 4,21-dichloro-6α,9α-difluoro-11β-hydroxy-16α,17α-isopropylidenedioxypregna-1,4-diene-3,20-dione, mp 286°-289° C., [α]$_D$+161° (pyridine), is obtained.

B. By following in principle the procedure of Part A of this example but substituting an appropriate starting material as set forth in the "Preparation of Starting Compounds" section for fluocinolone acetonide the following compounds are obtained:

4-chloro-6α,9α,21-trifluoro-11β-hydroxy-16α,17α-isopropylidenedioxypregna-1,4-diene-3,20-dione;

4-chloro-6α,9α,21,21-tetrafluoro-11β-hydroxy-16α,17α-isopropylidenedioxypregna-1,4-diene-3,20-dione;

4,21,21-trichloro-6α,9α-difluoro-11β-hydroxy-16α,17α-isopropylidenedioxypregna-1,4-diene-3,20-dione;

4-chloro-6α,9α-difluoro-11β-hydroxy-16α,17α-isopropylidenedioxy-21,21-dimethoxypregna-1,4-diene-3,20-dione;

4-chloro-6α,9α-difluoro-11β,21-dihydroxy-16α,17α-isopropylidenedioxypregna-1,4-diene-3,20-dione;

4-chloro-6α,9α-difluoro-11β-hydroxy-16α,17α-isopropylidenedioxy-21-acetoxypregna-1,4-diene-3,20-dione;

4-chloro-6α,9α-difluoro-11β-hydroxy-16α,17α-isopropylidenedioxy-21-propionyloxypregna-1,4-diene-3,20-dione; and the like.

EXAMPLE 4

This example sets forth a process for preparing 4,9α,11β-trichloro-6α-fluoro-16α,17α-isopropylidenedioxypregna-1,4-diene-3,20-dione (which are substituted at the 21 position similarly to Example 2) according to the reaction sequence of Example 1 wherein X$^1$ and X$^3$ are chloro, X$^2$ is fluoro, and X$^4$ is

A. By following in principle the procedure of Example 2, Part A but substituting 9α,11α,21-trichloro-6α-fluoro-16α,17α-isopropylidenedioxypregna-1,4-diene-3,20-dione for 6α,21-difluoro-9α,11β-dichloro-16α,17α-isopropylidenedioxypregna-1,4-diene-3,20-dione and dichlorohydantoin for ClO$_3$F, 4,9α,11β-21-tetrachloro-6α-fluoro-16α,17α-isopropylidenedioxypregna-1,4-diene-3,20-dione, mp 256°-259° C., [α]$_D$+183° (CHCl$_3$), is obtained.

B. By following in principle the procedure of Part A of this example, but substituting an appropriate starting material as prepared in the "Preparations of Starting Compounds" section, the following compounds are obtained:

4,9α,11β-trichloro-6α,21-difluoro-16α,17α-isopropylidenedioxypregna-1,4-diene-3,20-dione, mp 257.5°-258° C., $[\alpha]_D +102°$ (CHCl$_3$);

4,9α,11β-trichloro-6α,21,21-trifluoro-16α,17α-isopropylidenedioxypregna-1,4-diene-3,20-dione;

4,9α,11β,21,21-pentachloro-6α-fluoro-16α,17α-isopropylidenedioxypregna-1,4-diene-3,20-dione;

4,9α,11β,21-tetrachloro-6α-fluoro-16α,17α-isopropylidenedioxypregna-1,4-diene-3,20-dione;

4,9α,11β-trichloro-6α-fluoro-16α,17α-isopropylidenedioxy-21,21-dimethoxypregna-1,4-diene-3,20-dione;

4,9α,11β-trichloro-6α-fluoro-16α,17α-isopropylidenedioxy-21-hydroxypregna-1,4-diene-3,20-dione;

4,9α,11β-trichloro-6α-fluoro-16α,17α-isopropylidenedioxy-21-hexanoylhydroxypregna-1,4-diene-3,20-dione;

4,9α,11β-trichloro-6α-fluoro-16α,17α-isopropylidenedioxy-21-acetoxypregna-1,4-diene-3,20-dione, and the like

EXAMPLE 5

This example sets forth a process for preparing 4,9α-difluoro-6-chloro-11β-hydroxy-16α,17α-isopropylidenedioxypregna-1,4-diene-3,20-diones (which are substituted at the 21 position similarly to Example 2) according to the reaction sequence of Example 1 wherein $X^1$ and $X^3$ are fluoro, $X^2$ is chloro and $X^4$ is

A. 4,9α-Difluoro-6α-chloro-11β,21-dihydroxy-16α,17α-isopropylidenedioxypregna-1,4-diene-3,20-dione is prepared by following in principle the procedure set forth in Example 1, Part A, but substituting 6α-chloro-9α-fluoro-11β,21-dihydroxy-16α,17α-isopropylidenedioxypregna-1,4-diene-3,20-dione for fluocinolone acetonide.

B. By substituting other appropriate starting materials in the process of Part A of this example other compounds of this invention are prepared such as 4,9α-difluoro-6α,21-dichloro-11β-hydroxy-16α,17α-isopropylidenedioxypregna-1,4-diene-3,20-dione;

4,9α-difluoro-6α-chloro-11β-hydroxy-16α,17α-isopropylidenedioxy-21,21-dimethoxypregna-1,4-diene-3,20-dione; and the like.

EXAMPLE 6

This example sets forth a process for preparing 4-fluoro-6α,9α,11β-trichloro-11β-hydroxy-16α,17α-isopropylidenedioxypregna-1,4-diene-3,20-diones (which are substituted at the 21 position similarly to Example 2) according to the reaction sequence of Example 1 wherein $X^1$ is fluoro, $X^2$ and $X^3$ are both chloro and $X^4$ is

A. 4,21-Difluoro-6α,9α,11β-trichloro-16α,17α-isopropylidenedioxypregna-1,4-diene-3,20-dione is prepared by following in principle the procedure of Example 2, Part A but substituting 6α,9α,11β-trichloro-16α,17α-isopropylidenedioxy-21-fluoropregna-1,4-diene-3,20-dione for 6α,21-difluoro-9α,11β-dichloro-16α,17α-isopropylidenedioxypregna-1,4-diene-3,20-dione as the starting material.

B. By substituting other appropriate starting materials in the process of Part A of this example, other compounds of this invention are prepared such as 4-fluoro-6α,9α,11β-trichloro-16α,17α-isopropylidenedioxy-21-acetoxypregna-1,4-diene-3,20-dione;

4-fluoro-6α,9α,11β,21-tetrachloro-16α,17α-isopropylidenedioxypregna-1,4-dione; and the like.

EXAMPLE 7

By following in principle the process set forth in Example 1, Part A but deleting the acetylation step and substituting an appropriate 21-substituted 6α,9α-dichloro-11β-hydroxy-16α,17α-isopropylidenedioxypregna-1,4-diene-3,20-dione for fluocinolone acetonide, 4-fluoro-6α,9α-dichloro-11β-hydroxy-16α,17α-isopropylidene dioxypregna-1,4-diene-3,20-diones are prepared according to the reaction sequence of Example 1 wherein $R^1$ is hydrogen, fluoro, chloro, bromo, hydroxy or methoxy and $R^2$ is fluoro, chloro, bromo, hydroxy or alkanoyloxy of 2-6 carbons when $R^1$ is hydrogen, or $R^2$ is the same as $R^1$ when $R^1$ is fluoro, chloro or methoxy.

In this process, however, the conversion from the 4α-fluoro-6-chloropregna-1,5-diene to the corresponding 4-fluoro-6α-chloropregna-1,4-diene takes place under acid conditions instead of basic conditions set forth in Example 1. Thus, ten g of the compound represented by (IV$_1$) (wherein $R^1$ is hydrogen, $R^2$ is hydroxy, $X^1$ is fluoro, $X^2$ and $X^3$ are chloro, and $X^4$ is

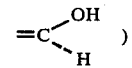

is placed in 100 ml CH$_3$OH along with one ml of concentrated HCl and the resulting mixture is refluxed for two hours. The reaction mixture is thereafter poured into about 500 ml water and the resulting precipitate is extracted with CH$_2$Cl$_2$. The CH$_2$Cl$_2$ solution is washed with three equal volumes of water, dried over anhydrous sodium sulfate, concentrated to dryness and the resulting precipitate is purified using column chromatography to give 4-fluoro-6α,9α-dichloro-11β-hydroxy-16α,17α-isopropylidenedioxy-21-hydroxypregna-1,4-diene-3,20-dione.

EXAMPLE 8

By following in principle the process set forth in Example 7, but substituting an appropriate, 21-substituted 6α,9α-dichloro-11β-hydroxy-16α,17α-isopropylidenedioxypregna-1,4-diene-3,20-dione for 21-chloro-6α,9α-difluoro-11β-hydroxy-16α,17α-isopropylidenedioxypregna-1,4-diene-3,20-dione and dichlorohydantoin for ClO$_3$F, the desired 4,6α9α-trichloro-11β-hydroxy-16α,17α-isopropylidenedioxypregna-1,4-diene-3,20-diones are prepared according to the reaction sequence of Example 1 wherein $R^1$ is hydrogen, fluoro, chloro, bromo, hydroxy or methoxy and $R^2$ is fluoro, chloro, bromo, hydroxy or alkanoyloxy of 2-6 carbons when $R^1$ is hydrogen or is the same as $R^1$ when $R^1$ is fluoro, chloro or methoxy.

EXAMPLE 9

This example sets forth a process for preparing 21-substituted 4,6α-difluoro-11β-hydroxy-16α,17α-isopropylidenedioxypregn-4-ene-3,20-diones according to the following reaction sequence:

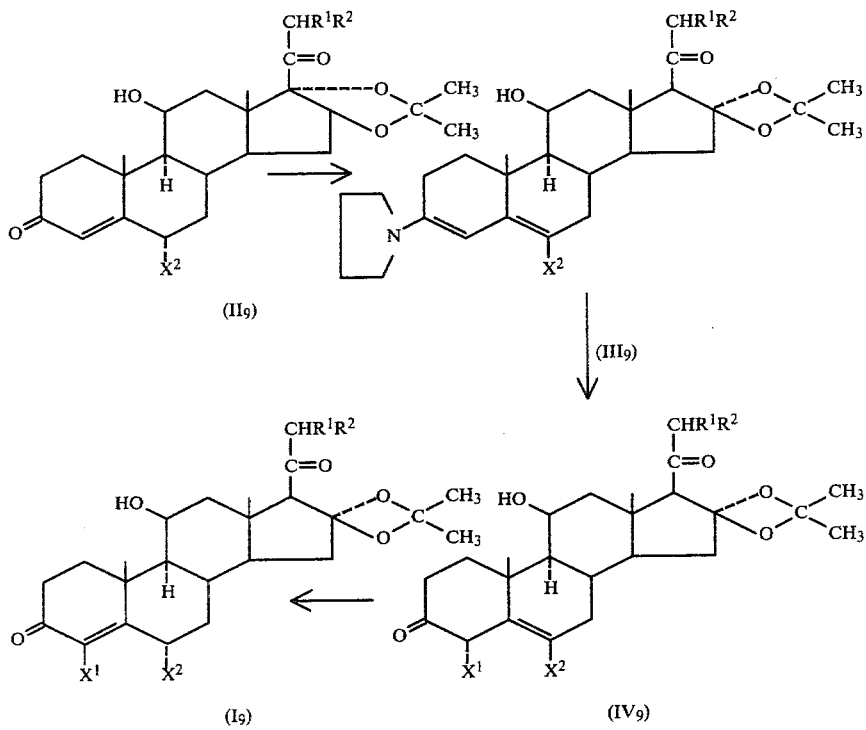

wherein $R^1$ and $R^2$ are as defined in Example 8 and $X^1$ and $X^2$ are both fluoro.

Ten g of a compound of formula (II$_9$) are mixed with 100 ml benzene and refluxed in the presence of a slight molar excess of pyrrolidine until TLC analysis indicates that the reaction is complete. Excess benzene and pyrrolidine are eliminated under reduced pressure to leave a residue of an enamine represented by formula (III$_9$) which is purified by crystallization from a suitable organic solvent or by chromatography using alumina.

One g of compound of formula (III)$_9$ is dissolved in 10 ml pyridine and the resulting solution is cooled to 0° C., then perchloryl fluoride, is slowly bubbled into the reaction mixture, until TLC analysis indicates the reaction is complete. The mixture is then concentrated under reduced pressure to give a crude residue of a compound represented by formula (IV$_9$) which is purified by crystallization from a suitable solvent or by chromatography on silica gel.

Five hundred (500) mg of a compound represented by formula (IV$_9$) is dissolved in MeOH or a mixture of MeOH and dichloromethane, under a nitrogen atmosphere and a catalytic amount (20% of an equivalent) of anhydrous potassium carbonate is added. The reaction mixture is stirred at room temperature until TLC analysis indicates the reaction is complete. Upon completion of the reaction, glacial acetic acid is added to destroy excess potassium carbonate, the mixture is concentrated, the mixture is concentrated under reduced pressure to a small volume and water is added thereto to give a crystalline precipitate of a compound represented by formula (I$_9$). If a C-21 acetate is present in the starting material, it will be hydrolyzed to the corresponding C-21 alcohol.

By substituting dichlorohydantoin for ClO$_3$F in this example, the corresponding 4-chloro steroid is obtained.

EXAMPLE 10

By following in principle the procedure and reaction sequence of Example 9, 21-substituted 4,6α-dichloro-11β-hydroxy-16,17α-isopropylidenedioxypregn-4-ene-3,20-diones are prepred wherein $X^1$ and $X^2$ are both chloro.

In this reaction sequence, however, to convert a compound represented by formula (III$_9$) to one of formula (IV) dichlorohydantoin is substituted for perchloryl fluoride. Thus, a compound of formula (III$_9$) is dissolved in a mixture of 90% acetone and 10% water and reacted with 1.1 equivalents of dichlorohydantoin at room temperature for about 30 minutes. The resulting mixture is diluted with water and the acetone is eliminated by distillation under reduced pressure to give a crystalline precipitate which is extracted with CH$_2$Cl$_2$ and purified as discussed in Example 9.

EXAMPLE 11

This example sets forth a process for preparing 4,6α,-9α-trifluoro-11α,17α,21-trihydroxy-16α-methylpregna-1,4-diene-3,20-diones according to the following reaction sequence:

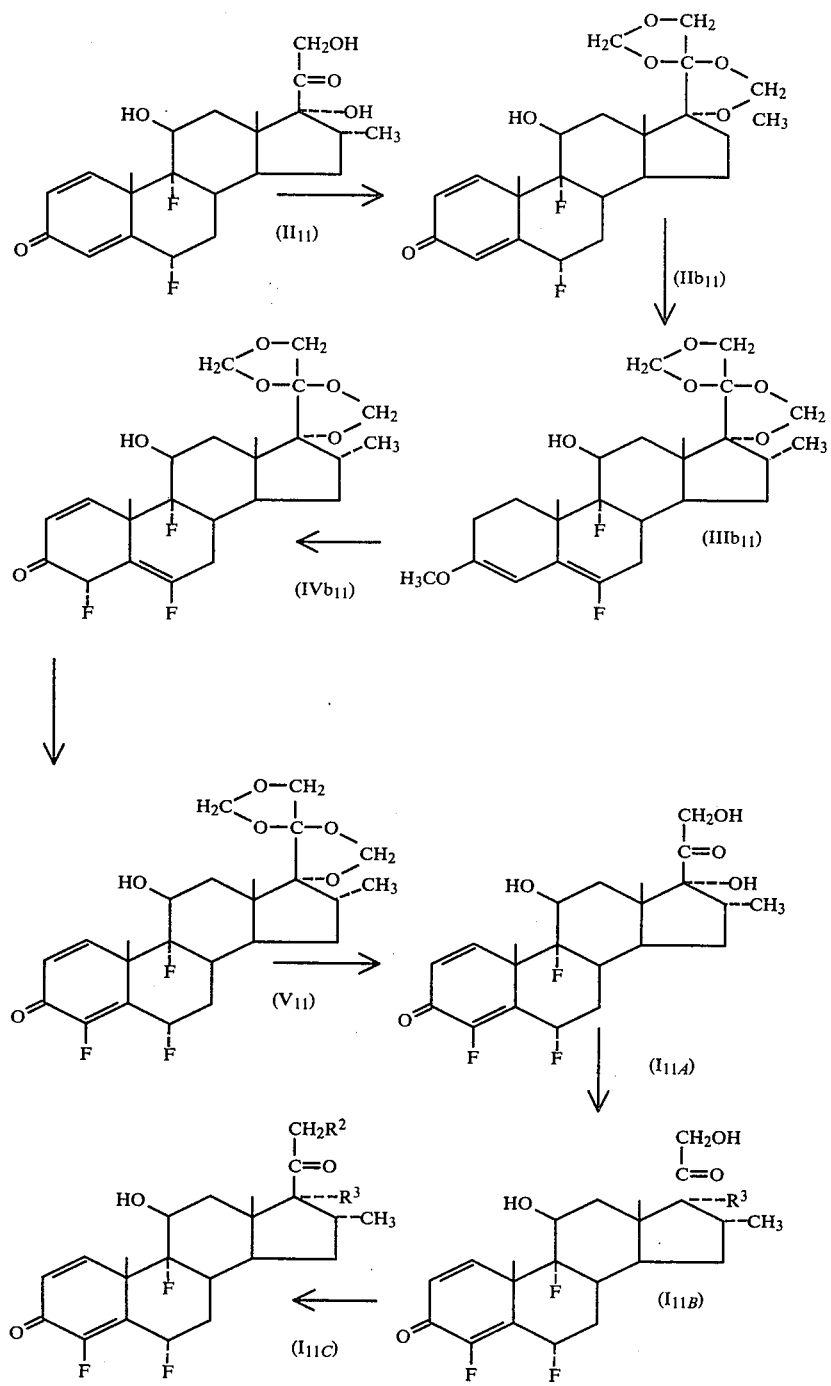

wherein $R^2$ is alkanoyloxy of 2-6 carbon atoms, fluoro, chloro or bromo and $R^3$ is alkanoyloxy of 2-6 carbon atoms.

A. 4,6α,9α-Trifluoro-11β,17α,21-trihydroxy-16α-methylpregna-1,4-diene-3,20-dione.

Flumethasone (6α,9α-difluoro-11β,17α,21-trihydroxy-16α-methylpregna-1,4-diene-3,20-dione: 8 grams) is stirred into 200 milliliters (ml) of chloroform, and 50 g of paraformaldehyde and 120 ml of conc. HCl in 120 ml of water. (The paraformaldehyde solution is warmed to achieve dissolution.) The mixture is stirred for 48 hours at ambient temperature and the two layers are separated. The aqueous layer is extracted with chloroform, and the combined organic layer and chloroform extracts are washed with water to neutrality, dried over sodium sulfate and evaporated to dryness to yield the 17,20:20,21-bismethylenedioxy (BMD) derivative of flumethasone (IIb₁₁) which is recrystallized from methanol:ether.

To a solution of 620 ml trimethyl orthoformate, 206 ml anhydrous methanol, and 4.1 ml fuming sulfuric acid, is added 41 g of the BMD derivative of flumethasone prepared according to the preceeding paragraph. The resulting mixture is warmed to 40°-50° for 30 minutes, at which time thin layer chromatography (TLC) using an eluant of 35% ethyl acetate and 65% hexane shows that the reaction is complete. Twenty-five ml of triethyl amine are added to neutralize the acid and the solvents are removed using a rotary evaporator at reduced pressure. The residue is dissolved in 500 ml of acetone, about 240 ml water is added and the acetone is removed under reduced pressure to give crystalline precipitate which is collected by filtration and air dried overnight to give 50 g of a compound represented by formula (IIIb$_{11}$), which is recrystallized from methanol-water.

The resulting product (10 g) is added to 300 ml of a solvent consisting of 90% acetone and 10% water and a slow stream of perchloryl fluoride (ClO$_3$F) is added at ambient temperature over about 30 minutes. TLC of the reaction mixture using a mixture of 35% ethyl acetate and 65% hexane shows the reaction to be complete upon completion of the ClO$_3$F addition. Water is slowly added to the reaction mixture until a total volume of 2 l is obtained. The mixture is concentrated under reduced pressure to give a crystalline precipitate which is collected by filtration, dissolved in methylene chloride (CH$_2$Cl$_2$) and the resulting solution is dried over anhydrous sodium sulfate. The solution is chromatographed on silica gel using methylene chloride/hexane and homogeneous fractions are collected and concentrated to dryness to give the product represented by Formula (IVb$_{11}$).

Five g of the resulting product is stirred with 100 ml methanol and 100 ml CH$_2$Cl$_2$ containing 1 g of anhydrous potassium carbonate under nitrogen at atmospheric pressure and ambient temperature for one hour, at which time TLC shows the reaction is complete. The reaction mixture is diluted with 100 ml methanol and 10 ml glacial acetic acid and concentrated under reduced pressure to a small volume. The crystalline precipitate which forms is collected by filtration and washed with methanol and water to give the BMD product represented by formula (V$_{12}$). One g of the BMD compound is mixed with 20 ml of 60% formic acid and heated on a steam bath for 1 hour. The mixture is cooled, diluted with water, and the resulting precipitate is filtered, water washed, dried and recrystallized from acetone:-hexane to yield 4,6α,9α-trifluoro-11β,17α,21-trihydroxy-16α-methylpregna-1,4-diene-3,20-dione.

B. 4,6α,9α-Trichloro-11β,17α,21-trihydroxy-16α-methylpregna-1,4-diene-3,20-dione 17 alkanoates Three hundred (300) mg. of 4,6α,9α-trifluoro-11β,17α,21-trihydroxy-16α-methylpregna-1,4-diene-3,2-dione are added to a 50 ml flask along with 5 ml of triethyl orthopropionate and a few mg of dried p-toluenesulfonic acid (pTSA). The mixture is stirred for 1 hour under nitrogen at 120° C. in an oil bath until the reaction is complete. Fifty ml of ethyl acetate along with 100 ml of water are mixed with the reaction mixture. After separating the water from the resulting organic phase, the latter is washed three times with 50 ml portions of water. The resulting organic mixture is dried over sodium sulfate, stripped and vacuum dried to give a yellow oil. The material is purified by preparative TLC. Extraction and crystallization from a suitable solvent ultimately gives 4,6α,9α-trifluoro-11α,17α,21-trihydroxy-16α-methylpregna-1,4-triene-3,20-dione 17,21-ethyl orthopropionate.

One hundred eighty mg of the resulting 17,21-ethyl orthopropionate, 6 ml of methanol and 1 ml of potassium hydrogen phosphate buffer (pH 3.1) are added to a 50 ml flask. The mixture is stirred overnight (approximately 17 hours) at room temperature which results in about 70% completion of the reaction. An additional 30 ml of methanol and 5 ml of potassium hydrogen phosphate buffer are added and the reaction is heated to 60° C. on a hot water bath for about 1 hour to bring the reaction to completion very cleanly. The reaction mixture is partitioned between ethyl and water and the ethyl acetate is removed by vacuum evaporation to give an oil which is then chromatographed using TLC to give 130 mg of 4,6α,9α-trifluoro-11β,17α,21-trihydroxy-16α-methylpregna-1,4-diene-3,20-dione 17-propionate.

By following the above procedure but substituting other suitable trialkyl orthoalkanoates such as trimethyl orthoacetate, trimethyl orthobutyrate, trimethyl orthovalerate, trimethyl orthohexanoate and the like for triethyl orthopropionate, other 17α-esters of this invention are prepared such as 4,6α,9α-trifluoro-11β,17α,21-trihydroxy-16α-methylpregna-1,4-diene-3,20-dione 17-acetate;

4,6α,9α-trifluoro-11β,17α,21-trihydroxy-16α-methylpregna-1,4-diene-3,20-dione 17-butyrate;

4,6α,9α-trifluoro-11β,17α,21-trihydroxy-16α-methylpregna-1,4-diene-3,20-dione 17-valerate;

4,6α,9α-trifluoro-11β,17α,21-trihydroxy-16α-methylpregna-1,4-diene-3,20-dione 17-hexanoate; and the like.

C. 4,6α,9α-trifluoro-11β,17α,21-trihydroxy-16α-methylpregna-1,4-diene-3,20-dione 17,21-dialkanoates.

Ninety-nine mg of the resulting 17α-propionate ester of Part B, above, is placed in a suitable flask along with 3 ml of pyridine and 0.2 ml of propionyl chloride and stirred for 2 hours at room temperature. The reaction mixture is then placed in the refrigerator overnight (about 17 hours) after which the reaction is complete. The reaction mixture is poured into dilute aqueous sodium carbonate and extracted with ethyl acetate. The organic phase is washed another time with dilute aqueous sodium carbonate, then four times with water, dried over sodium sulfate and the solvent is removed by vacuum evaporation. The product is purified by chromatography using TLC to afford 4,6α,9α-trifluoro-11β,17α,21-trihydroxy-16α-methylpregna-1,4-diene-3,20-dione 17-21-dipropionate.

Similarly by employing other alkanoyl chlorides such as acetyl chloride, butyryl chloride, valeryl chloride and hexanoyl chloride for propionyl chloride and/or other 17α-alkanoates of Part B of this Example for 17α-propionate, other 17α,21-diesters of this invention are prepared such as 4,6α,9α-trifluoro-11β,21-trihydroxy-16α-methylpregna-1,4-diene-3,20-dione 17-propionate 21-acetate;

4,6α,9α-trifluoro-11β,17α,21-trihydroxy-16α-methylpregna-1,4-diene-3,20-dione 17-propionate 21-butyrate;

4,6α,9α-trifluoro-11β,17α,21-trihydroxy-16α-methylpregna-1,4-diene-3,20-dione 17-propionate 21-valerate;

4,6α,9α-trifluoro-11β,17α,21-trihydroxy-16α-methylpregna-1,4-diene-3,20-dione 17-propionate 21-hexanoate; and the like.

D. 4,6α,9α-trifluoro-11β,17α,21-trihydroxy-16α-methyl-21-halopregna-1,4-diene-3,20-dione 17-alkanoates.

The 4,6α,9α-trifluoro-11β,17α,21-trihydroxy-16α-methylpregna-1,4-diene-3,20-dione 17-propionate prepared in Part B of this Example is dissolved in pyridine and a molar excess of methanesulfonyl chloride is added at 0° C. After standing in a refrigerator until TLC indicates the reaction is complete, excess methanesulfonyl chloride is destroyed by the addition of small amount of ice, after which ice-water is slowly added to precipitate the reaction product. The resulting 21-mesylate is filtered, washed with water, dried in vacuo and recrystallized.

The resulting 21-mesylate is treated with a molar excess of lithium chloride in dimethylformamide at an elevated temperature (about 100° C.) until TLC shows the reaction to be complete. The reaction mixture is poured onto ice, extracted with chloroform and the chloroform extract is washed with water and dried over sodium sulfate. Evaporation of the solvent in vacuo gives 4,6α,9α-trifluoro-11β,17α-dihydroxy-16α-methyl-21-chloropregna-1,4-diene-3,20-dione 17-propionate.

By following this procedure but substituting lithium bromide for lithium chloride, 4,6α-9α-trifluoro-11β,17α-dihyroxy-16α-methyl-21-bromopregna-1,4-diene-3,20-dione is obtained.

By heating at 135° C. the 21-mesylate with potassium fluoride and sulfolane until TLC indicates the reaction is complete, then extracting and crystallizing according to methods known in the art, the compound 4,6α,9α,21-tetrafluoro-11β,17α-dihydroxy-16α-methylpregna-1,4-diene-3,20-dione is obtained.

By following the above procedures for preparing the 21-chloro and 21-fluoro compounds but substituting other 17-alkanoates prepared for 4,6α,9α,21-trifluoro-11α,17α-dihydroxy-16α-methylpregna-1,4-diene-3,20-dione 17-propionate, other compounds of this invention are obtained such as 4,6α,9α-trifluoro-11β,17α-dihydroxy-16α-methyl-21-chloropregna-1,4-diene-3,20-dione 17-acetate;
4,6α,9α-trifluoro-11α,17α-dihydroxy-16α-methyl-21-chloropregna-1,4-diene-3,20-dione 17-butyrate;
4,6α,9α-trifluoro-11β,17β-dihydroxy-16α-methyl-21-chloropregna-1,4-diene-3,20-dione 17-valerate;
4,6α,9α-trifluoro-11β,17α-dihydroxy-16α-methyl-21-chloropregna-1,4-diene-3,20-dione 17-hexanoate;
4,6α,9α,21-tetrafluoro-11β,17α-dihydroxy-16α-methyl-pregna-1,4-diene-3,20-dione 17-acetate;
4,6α,9α,21-tetrafluoro-11β,17α-dihydroxy-16α-methylpregna-1,4-diene-3,20-dione 17-butyrate;
4,6α,9α,21-tetrafluoro-11β,17α-dihydroxy-16α-methylpregna-1,4-diene-3,20-dione 17-valerate;
4,6α,9α,21-tetrafluoro-11β,17α-dihydroxy-16α-methylpregna-1,4-diene-3,20-dione 17-hexanoate; and the like.

EXAMPLE 12

A. 4,6α-Difluoro-11β,17α,21-trihydroxy-16α-methylpregna-1,4-diene-3,20-dione

6α-Fluoro-11β,17α,21-trihydroxy-16α-methylpregn-4-ene-3,20-dione is converted to 4,6α-difluoro-11β,17α,21-trihydroxy-16α-methylpregn-4-ene-3,20-dione by following in principle the process set forth in Example 9. This compound, in turn is converted to the corresponding pregna-1,4-diene compound according to the following procedure:

A mixture of 0.5 g. of 4,6α-difluoro-11β,17α,21-trihydroxy-16α-methylpregn-4-ene-3,20-dione, 10 ml. of dioxane and 0.35 g. of 2,3-dichloro-5,6-dicyano-1,4-benzoquinone is refluxed for 20 hours. The mixture is then cooled, filtered and evaporated to dryness. The residue is dissolved in acetone and this solution is then filtered through 10 g. of alumina and concentrated to yield 4,6α-difluoro-11β,17α,21-trihydroxy-16α-methylpregna-1,4-diene-3,20-dione which is further purified by recrystallization from acetone:hexane.

B. 4,6α-Difluoro-11β,17α,21-trihydroxy-16α-methylpregna-1,4-diene-3,20-dione 17-alkanoates By following in principle the procedure of Example 11, Part B, but substituting 4,6α-difluoro-11β,17α,21-trihydroxy-16α-methylpregna-1,4-diene-3,20-dione for 4,6α,9α-trifluoro-11β,17α,21-trihydroxy-16α-methylpregna-1,4-diene-3,20-dione, the following 17-alkanoates are obtained:

4,6α-difluoro-11β,17α,21-trihydroxy-16α-methylpregna-1,4-diene-3,20-dione 17-acetate;
4,6α-difluoro-11β,17α,21-trihydroxy-16α-methylpregna-1,4-diene-3,20-dione 17-propionate;
4,6α-difluoro-11β,17α,21-trihydroxy-16α-methylpregna-1,4-diene-3,20-dione 17-butyrate;
4,6α-difluoro-11β,17α,21-trihydroxy-16α-methylpregna-1,4-diene-3,20-dione 17-valerate;
4,6α-difluoro-11β,17α,21-trihydroxy-16α-methylpregna-1,4-diene-3,20-dione 17-hexanoate; and the like.

C. 4,6α-Difluoro-11β,17α,21-trihydroxy-16α-methylpregna-1,4-diene-3,20-dione 17,21-dialkanoates By following in principle the procedure of Example 11, Part C, but employing the 17-alkanoates of Part B of this Example other 17,21-dialkanoates are obtained such as 4,6α-difluoro-11β,17α,21-trihydroxy-16α-methylpregna-1,4-diene-3,20-dione 17-acetate 21-propionate;
4,6α-difluoro-11β,17α,21-trihydroxy-16α-methylpregna-1,4-diene-3,20-dione 17,21-dipropionate;
4,6α-difluoro-11β,17α,21-trihydroxy-16α-methylpregna-1,4-diene-3,20-dione 17-butyrate 21-propionate;
4,6α-difluoro-11β,17α,21-trihydroxy-16α-methylpregna-1,4-diene-3,20-dione 17-valerate 21-propionate;
4,6α-difluoro-11β,17α,21-trihydroxy-16α-methylpregna-1,4-diene-3,20-dione 17-hexanoate 21-propionate; and the like.

D. 4,6α-Difluoro-11β,17α,21-trihydroxy-16α-methyl-21-halo pregna-1,4-diene-3,20-dione 17-alkanoate By following in principle the process of Part D of Example 11, but employing an appropriate compound named in Part B of this example, 21-halo 17-alkanoates of this invention are prepared such as 4,6α-difluoro-11β,17α-dihydroxy-16α-methyl-21-chloropregna-1,4-diene-3,20-dione 17-acetate;
4,6α-difluoro-11β,17α-dihydroxy-16α-methyl-21-chloropregna-1,4-diene-3,20-dione 17-propionate;
4,6α-difluoro-11β,17α-dihydroxy-16α-methyl-21-chloropregna-1,4-diene-3,20-dione 17-butyrate;
4,6α-difluoro-11β,17α-dihydroxy-16α-methyl-21-chloropregna-1,4-diene-3,20-dione 17-valerate;
4,6α-difluoro-11β,17α-dihydroxy-16α-methyl-21-chloropregna-1,4-diene-3,20-dione 17-hexanoate;
4,6α,21-trifluoro-11β,17α-dihydroxy-16α-methylpregna-1,4-diene-3,20-dione 17-acetate;
4,6α,21-trifluoro-11β,17α-dihydroxy-16α-methylpregna-1,4-diene-3,20-dione 17-propionate;
4,6α,21-trifluoro-11β,17α-dihydroxy-16α-methylpregna-1,4-diene-3,20-dione 17-butyrate;
4,6α,21-trifluoro-11β,17α-dihydroxy-16α-methylpregna-1,4-diene-3,20-dione 17-valerate;
4,6α,21-trifluoro-11β,17α-dihydroxy-16α-methylpregna-1,4-diene-3,20-dione 17-hexanoate; and the like.

EXAMPLE 13

A. 4-fluoro-9,11-epoxy-16α-methyl-17α,21-dihydroxypregna-1,4-diene-3,20-dione 21-acetate 4,6α-Difluoro-11β,17α,21-trihydroxy-16α-methyl-pregn-4-ene-3,20-dione (of Example 12A) is converted to the corresponding 21-acetate by reaction with acetic anhydride and pyridine at room temperature.

One gram of the resulting 4,6α-difluoro-11β,17α-dihydroxy-16α-methyl-21-acetoxypregn-4-ene-3,20-dione is dissolved in 12.5 ml. of dimethylformamide as the solvent is slowly heated. The mixture is cooled and 0.42 g. of methanesulfonyl chloride and 0.5 ml. of pyridine is added. After heating the reaction mixture at 80° C. for 30 minutes, it is cooled, diluted with water and extracted with ethyl acetate. The extracts are washed with water, dried over sodium sulfate and evaporated to yield 4,6α-difluoro-17α-hydroxy-16α-methyl21-acetoxypregna-4,9(11)-diene-3,20-dione which is further purified by recrystallization from acetone:hexane.

The pregna-4,9(11)-diene is treated according to the procedure of Example 12A, paragraph 2 to give 4,6α-difluoro-17α-hydroxy-16α-methyl-21-acetoxypregna-1,4,9(11)-triene-3,20-dione.

The resulting compound is placed in dioxane (A.R.) along with a small portion of a solution of 70% $HClO_4$ in water and is treated with dibromohydantoin in the dark at room temperature for a period of one hour or when TLC using 50% ethyl acetate/50% hexane shows the reaction to be complete. The reaction mixture is precipitated in water, stirred for 10 minutes and the crystalline precipitate collected by filtration, washed with water, and air dried to give 4,6α-difluoro-9α-bromo-11β,17α-dihydroxy-16α-methyl21-acetoxypregna-1,4-diene-3,20-dione.

The resulting 9,11-bromohydrin of this example is stirred with methanol containing anhydrous potassium carbonate under nitrogen until TLC shows the reaction is complete. The reaction mixture is diluted with methanol and glacial acetic acid and concentrated under reduced pressure to a small volume. The precipitate is collected by filtration and washed with methanol and water to give 4,6α-difluoro-9,11-epoxy-16α-methyl-17α,21-dihydroxypregna-1,4-diene-3,20-dione. This product, in turn is reacted with acetic anhydride in pyridine at room temperature for 15 hours (or until TLC shows the reaction is complete). The mixture is then poured into ice water and the solid which forms is collected by filtration, washed with water and dried to yield 4,6α-difluoro-9,11-epoxy-16α-methyl-17α,21-dihydroxypregna-1,4-diene-3,20-dione 21-acetate which is further purified through recrystallization from acetone:hexane.

Six hundred (600) mg of zinc metal dust containing 3% cupric acetate (previously blended with mortar and pestle) and 100 ml of a 1:1 mixture of dry methanol and methylene chloride are stirred together in a heat-dried nitrogen blanketed 500 ml three neck flask with septum addition funnel and magnetic stirrer. A solution of 2.0 g of 4,6α-difluoro-9,11-oxo-16α-methyl-17,21-dihydroxyprenga-1,4-diene-3,20-dione 21-acetate in 120 ml of 1:1 methanol-methylene chloride solvent mixture is placed in the addition funnel and 0.6 ml of glacial acetic acid is added to zinc slurry via syringe and stirred together for 20 minutes, after which all of the solution of oxide is added from the addition funnel.

After 2½ hours, the reaction mixture is cooled in ice, then filtered through a cake of celite, washed through with the methanol-methylene chloride solvent mixture. The pH of the filtrate is adjusted for pH 7 with a solution of 1.5% $K_2CO_3$ in methanol containing 10% water. The transient 1,5-diene intermediate spontaneously rearranges to the 1,4-diene in neutral solution and the methanol and methylene chloride are then evaporated while ethyl acetate is added to replace them. The ethyl acetate solution is washed three times with water, then dried over sodium sulfate and subsequently is stripped to dryness.

The residue is applied to a silica gel column prepared in 1% methanol-methylene chloride and is developed by gradient elution up to 4% methanol-methylene chloride. Recovery of material from the appropriate fractions and recrystallization from acetone-hexane affords 4-fluoro-9,11-epoxy-16α-methyl-17α,21-dihydroxypregna-1,4-diene-3,20-dione 21-acetate.

B.  4,9α-difluoro-11β,17α,21-trihydroxy-16α-methyl-pregna-1,4-diene-3,20-dione

The resulting 9,11-epoxide is treated with hydrogen fluoride in the presence of boron trifluoride and THF in $CH_2Cl_2$ to give the corresponding 4,9α-difluoro-11β,17α-dihydroxy-16α-methyl-21-acetoxypregna-1,4-dien-3,20-dione. This compound in turn is treated with anhydrous potassium carbonate in the presence of methanol under nitrogen at atmospheric pressure and ambient temperature until TLC shows the reaction is complete. The reaction mixture is diluted with methanol and glacial acetic acid then concentrated under reduced pressure to a small volume. The resulting crystalline precipitate is collected by filtration and washed with methanol and water to give 4,9α-difluoro-11β,17α,21-trihydroxy-16α-methylpregna-1,4-diene-3,20-dione.

C.  4,9α-Difluoro-11β,17α,21-trihydroxy-16α-methylpregna-1,4-diene-3,20-dione 17-alkanoates By following in principle the procedure of Example 11, Part B, but employing suitable trialkyl orthoalkanoates such as trimethyl orthoacetate, triethyl orthopropionate, trimethyl orthobutyrate, trimethyl orthovalerate and trimethyl orthohexanoate and the like, other 17α-esters of this invention are prepared such as 4,9α-difluoro-11β,17α,21-trihydroxy-16α-methyl-pregna-1,4-diene-3,20-dione 17-acetate;

4,9α-difluoro-11β,17α,21-trihydroxy-16α-methyl-pregna-1,4-diene-3,20-dione 17-propionate;

4,9α-difluoro-11β,17α,21-trihydroxy-16α-methyl-pregna-1,4-diene-3,20-dione 17-butyrate;

4,9α-difluoro-11β,17α,21-trihydroxy-16α-methyl-pregna-1,4-diene-3,20-dione 17-valerate; and 4,9α-difluoro-11β,17α,21-trihydroxy-16α-methyl-pregna-1,4-diene-3,20-dione 17-hexanoate; and the like.

D.  4,9α-Difluoro-11β,17α,21-trihydroxy-16α-methylpregna-1,4-diene-3,20-dione 17,21-dialkanoates By following in principle the procedure of Example 11, Part C but employing alkanoyl chloride such as acetyl chloride, propionyl chloride, butyryl chloride, valeryl chloride and hexanoyl chloride and the 17-alkanoates, e.g. the 17-propionate, of Part C of this Example, other compounds of this invention are obtained, such as 4,9α-difluoro-11β,17α,21-trihydroxy-16α-methyl-pregna-1,4-diene-3,20-dione 17-propionate 21-acetate;

4,9α-difluoro-11β,17α,21-trihydroxy-16α-methyl-pregna-1,4-diene-3,20-dione 17,21-dipropionate;

4,9α-difluoro-11β,17α,21-trihydroxy-16α-methyl-pregna-1,4-diene-3,20-dione 17-propionate 21-butyrate;

4,9α-difluoro-11β,17α,21-trihydroxy-16α-methyl-pregna-1,4-diene-3,20-dione 17-propionate 21-valerate;

4,9α-difluoro-11β,17α,21-trihydroxy-16α-methyl-pregna-1,4-diene-3,20-dione 17-propionate 21-hexanoate; and the like.

E. 4,9α-Difluoro-11β,17α,21-trihydroxy-16α-methyl-21-halo-1,4-diene-3,20-dione 17-alkanoates By following in principle the procedure of Example 11, Part D but substituting the appropriate 17-alkanoate-21-hydroxy compounds of Part C of this example, the following compounds are prepared:

4,9α-difluoro-11β,17α-dihydroxy-16α-methyl-21-chloropregna-1,4-diene-3,20-dione 17-acetate;

4,9α-difluoro-11β,17α-dihydroxy-16α-methyl-21-chloropregna-1,4-diene-3,20-dione 17-propionate;

4,9α-difluoro-11β,17α-dihydroxy-16α-methyl-21-chloropregna-1,4-diene-3,20-dione 17-butyrate;

4,9α-difluoro-11β,17α-dihydroxy-16α-methyl-21-chloropregna-1,4-diene-3,20-dione 17-valerate;

4,9α-difluoro-11β,17α-dihydroxy-16α-methyl-21-chloropregna-1,4-diene-3,20-dione 17-hexanoate;

4,9α,21-trifluoro-11β,17α-dihydroxy-16α-methylpregna-1,4-diene-3,20-dione 17acetate;

4,9α,21-trifluoro-11β,17α-dihydroxy-16α-methylpregna-1,4-diene-3,20-dione 17-propionate;

4,9α,21-trifluoro-11β,17α-dihydroxy-16α-methylpregna-1,4-diene-3,20-dione 17-butyrate;

4,9α,21-trifluoro-11β,17α-dihydroxy-16α-methylpregna-1,4-diene-3,20-dione 17-valerate;

4,9α,21-trifluoro-11β,17α-dihydroxy-16α-methylpregna-1,4-diene-3,20-dione 17-hexanoate; and the like.

EXAMPLE 14

A. 4-fluoro-9α-chloro-11β,17α,21-trihydroxy-16α-methylpregna-1,4-diene-3,20-dione To a stirred solution of 4 g of 4-fluoro-9,11-expoxy-16α-methyl-17α,21-dihydroxypregna-1,4-diene-3,20-dione 21-acetate (prepared as in Example 13A) 40 ml of anhydrous chloroform, are added over a period of 35 minutes and at 0° C., 30 ml of a 0.45 N chloroform solution of dry hydrogen chloride. The mixture is stirred for 1 hour at 0° C. and then diluted with water. The organic layer is separated, washed with aqueous sodium bicarbonate solution and with water, dried over sodium sulfate and evaporated under reduced pressure to yield 4-fluoro-9α-chloro-11β,17α,21-trihydroxy-16α-methylpregna-1,4-diene-3,20-dione 21-acetate which is recrystallized from acetone:hexane.

This compound is treated with potassium carbonate in anyhydrous methanol under nitrogen according to the procedure of Example 13A to obtain 4-fluoro-9α-chloro-11β,17α,21-trihydroxy-16α-methylpregna-1,4-diene-3,20-dione.

B. 4-fluoro-9α-chloro-11β,17α,21-trihydroxy-16α-methylpregna-1,4-diene-3,20-dione 17 alkanoates By following in principle the procedure of Example 11B but reacting the 4-fluoro-9α-chloro-11β,17α,21-trihydroxy-16α-methylpregna-1,4-diene-3,20-dione with other trialkyl orthoalkanoates (including triethyl orthopropionate), the following compounds of the invention are obtained:

4-fluoro-9α-chloro-11β,17α,21-trihydroxy-16α-methylpregna-1,4-diene-3,20-dione 17 acetate 4-fluoro-9α-chloro-11β,17α,21-trihydroxy-16α-methylpregna-1,4-diene-3,20-dione 17-propionate;

4-fluoro-9α-chloro-11β,17α,21-trihydroxy-16α-methylpregna-1,4-diene-3,20-dione 17-butyrate;

4-fluoro-9α-chloro-11β,17α,21-trihydroxy-16α-methylpregna-1,4-diene-3,20-dione 17-valerate;

4-fluoro-9α-chloro-11β,17α,21-trihydroxy-16α-methylpregna-1,4-diene-3,20-dione 17-hexanoate; and the like.

C. 4-fluoro-9α-chloro-11β,17α,21-trihydroxy-16α-methylpregna-1,4-diene-3,20-dione 17,21-dialkanoates By following in principle the procedure of Example 11C but reacting an appropriate 17-alkanoate, e.g. the 17-propionate, with other appropriate alkanoyl chlorides (including propionyl chloride), other compounds of this invention are obtained such as:

4-fluoro-9α-chloro-11β,17α,21-trihydroxy-16α-methylpregna-1,4-diene-3,20-dione 17-propionate 21-acetate;

4-fluoro-9α-chloro-11β,17α,21-trihydroxy-16α-methylpregna-1,4-diene-3,20-dione 17,21-dipropionate;

4-fluoro-9α-chloro-11β,17α,21-trihydroxy-16α-methylpregna-1,4-diene-3,20-dione 17-propionate 21-butyrate;

4-fluoro-9α-chloro-11β,17α,21-trihydroxy-16α-methylpregna-1,4-diene-3,20-dione 17-propionate 21-valerate;

4-fluoro-9α-chloro-11β,17α,21-trihydroxy-16α-methylpregna-1,4-diene-3,20-dione 17-propionate 21-hexanoate; and the like.

D. 4-fluoro-9α-chloro-11β,17α,21-trihydroxy-16α-methyl-21-halopregna-1,4-diene-3,20-dione 17-alkanoates By following in principle the procedures of Part D of Example 11 and using the appropriate 17-alkanoates of Part B of this example, the following compounds are prepared:

4-fluoro-9α,21-dichloro-11β,17-dihydroxy-16α-methylpregna-1,4-diene-3,20-dione 17acetate;

4-fluoro-9α,21-dichloro-11β,17-dihydroxy-16α-methylpregna-1,4-diene-3,20-dione 17-propionate;

4-fluoro-9α,21-dichloro-11β,17-dihydroxy-16α-methylpregna-1,4-diene-3,20-dione 17-butyrate;

4-fluoro-9α,21-dichloro-11β,17-dihydroxy-16α-methylpregna-1,4-diene-3,20-dione 17-valerate;

4-fluoro-9α,21-dichloro-11β,17-dihydroxy-16α-methylpregna-1,4-diene-3,20-dione 17-hexanoate;

4,21-difluoro-9α-chloro-11β,17α-dihydroxy-16-methylpregna-1,4-diene-3,20-dione 17-acetate;

4,21-difluoro-9α-chloro-11β,17α-dihydroxy-16-methylpregna-1,4-diene-3,20-dione 17-propionate;

4,21-difluoro-9α-chloro-11β,17α-dihydroxy-16-methylpregna-1,4-diene-3,20-dione 17-butyrate;

4,21-difluoro-9α-chloro-11β,17α-dihydroxy-16-methylpregna-1,4-diene-3,20-dione 17-valerate;

4,21-difluoro-9α-chloro-11β,17α-dihydroxy-16-methylpregna-1,4-diene-3,20-dione 17-hexanoate; and the like.

EXAMPLE 15

The example sets forth a process for preparing 4,6α-difluoro-9α,11β-dichloro-16α-methyl-17α-hydroxypregna-1,4-diene-3,20-diones according to the following reaction sequence wherein $X^1$ and $X^2$ are fluoro, $X^3$ is chloro and $X^4$ is

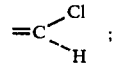

and $R^2$ is fluoro, chloro, bromo, methoxy, hydroxy or alkanoyloxy of 2-6 carbon atoms:

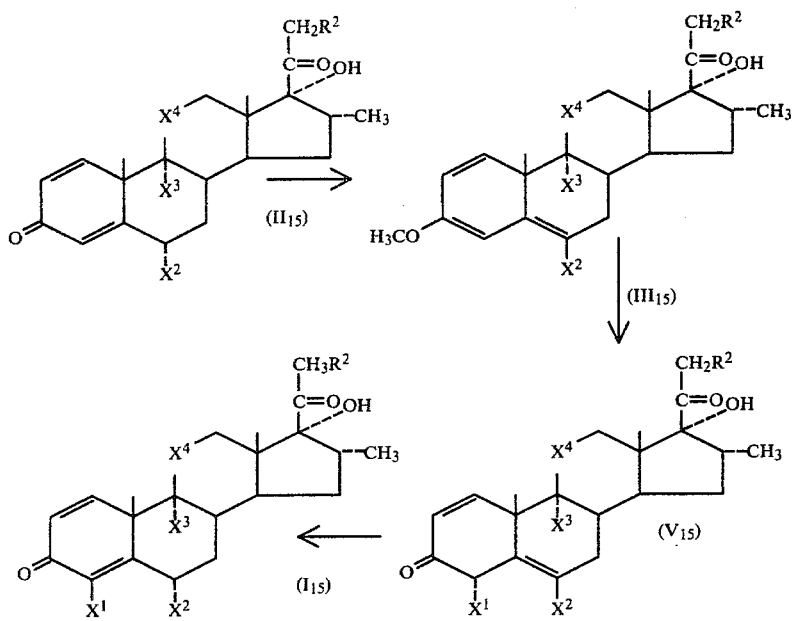

A. 4,6α,21-trifluoro-9α,11β-dichloro-16α-methyl-17α-hydroxypregna-1,4-diene-3,20-dione.

To a solution of 620 ml trimethyl orthoformate, 206 ml anhydrous methanol, and 4.1 ml fuming sulfuric acid, 41 g of 6α,21-difluoro-9α,11β-dichloro-16α-methyl-17α-hydroxypregna-1,4-diene-3,20-dione is added. The resulting mixture is heated to 40°–55° for 30 minutes, at which time TLC using an eluant of 35% ethyl acetate and 65% hexane shows that the reaction is complete. Twentyfive ml of triethylamine are added to neutralize the acid and the solvents are removed using a rotary evaporator at reduced pressure. The residue is dissolved in 500 ml of acetone, about 25 ml water is added and the acetone is removed under reduced pressure to give a crystalline precipitate which is collected by filtration and air dried overnight. The solid is dissolved in 400 ml of 75% methylene chloride/25% hexane and adsorbed on a column of 400 g silica gel. Continued elution with 80% methylene chloride/20% hexane, pure methylene chloride, then methylene chloride containing varying concentrations of ethyl acetate to give a series of portions which were combined then evaporated to leave about 12 g of a compound, represented by formula (III$_{15}$) wherein R$^2$ is fluoro.

The resulting product (10 g) is added to 300 ml of a mixture of 80% tetrahydrofuran and 20% water and a slow current of perchloryl fluoride (ClO$_3$F) is bubbled through the reaction mixture at ambient temperature over about 30 minutes. TLC of the reaction mixture using a mixture of 35% ethylacetate and 65% hexane shows the reaction to be complete upon completion of the ClO$_3$F addition. Water is slowly added to the reaction mixture until a total volume of 600 ml is obtained. The solvent acetone is eliminated under reduced pressure and the crystalline material is collected by filtration and purified by chromatography over a silica gel using a solvent mixture consisting of CH$_2$Cl$_2$ and hexane.

The resulting product (1 g) is stirred with 20 ml methanol and 20 ml CH$_2$Cl$_2$ containing 200 mg of anhydrous potassium carbonate in an inert atmosphere (nitrogen) at atmospheric pressure and ambient temperature for one hour, at which time TLC shows the reaction is complete. The reaction mixture is diluted with 20 ml methanol and 2 ml glacial acetic acid and concentrated under reduced pressure to a small volume. The crystalline precipitate which forms is collected by filtration and washed with methanol and water to give 0.5 g of the final product, namely 4,6α,21-trifluoro-9α,11β-dichloro-16α-methyl-17α-hydroxypregna-1,4-diene-3,20-dione.

B. By following in principle the procedure set forth in part A of this example and part A of Example 12, if appropriate, and using an appropriate starting material as prepared according to principles as set forth in the "Preparation of Starting Compounds" section, the following compounds are prepared:

4,6α,21,21-tetrafluoro-9α,11β-dichloro-16α-methyl-17α-hydroxypregna-1,4-diene-3,20-dione;

4,6α-difluoro-9α,11β,21,21-tetrachloro-16α-methyl-17α-hydroxypregna-1,4-diene-3,20-dione;

4,6α-difluoro-9α,11β,21-trichloro-16α-methyl-17α-hydroxypregna-1,4-diene-3,20-dione;

4,6α-difluoro-9α,11β-dichloro-16α-methyl-17α-hydroxy-21,21-dimethoxypregna-1,4-diene-3,20-dione;

4,6α-difluoro-9α,11β-dichloro-16α-methyl-17α,21-hydroxypregna-1,4-diene-3,20-dione;

4,6α-difluoro-9α,11β-dichloro-16α-methyl-17α-hydroxy-21-acetoxy-1,4-diene-3,20-dione; and the like.

EXAMPLE 16

This example sets forth a process for preparing 4,9α,11β-trichloro-6α-fluoro-11β,17α-dihydroxy-16α-methylpregna-1,4-diene-3,20-diones according to the reaction sequence of Example 15 wherein X$^1$ and X$^3$ are chloro, X$^2$ is fluoro and X$^4$ is

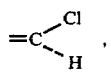

and R$^2$ is the same as in Example 15.

A. By following in principle the procedure of Example 15, Part A but substituting dichlorohydantoin for ClO₃F, 4,9α,11β-trichloro-6α,21-difluoro-16α-methyl-17α-hydroxypregna-1,4-diene-3,20-dione is obtained.

B. By following in principle the procedure of Part A of this example, but substituting an appropriate starting material according to the principles set forth in the "Preparation of Starting Compounds" section, the following compounds are obtained:

4,9α,11β-trichloro-6α,21-difluoro-16α-methyl-17α-hydroxypregna-1,4-diene-3,20-dione;

4,9α,11β-trichloro-6α-fluoro-16α-methyl-17α-hydroxy-21-bromopregna-1,4-diene-3,20-dione;

4,9α,11β,21-tetrachloro-6α-fluoro-16α-methyl-17α-hydroxypregna-1,4-diene-3,20-dione;

4,9α,11β-trichloro-6α-fluoro-16α-methyl-17α-hydroxy-21-dimethoxypregna-1,4-diene-3,20-dione;

4,9α,11β-trichloro-6α-fluoro-16α-methyl-17α,21-dihydroxypregna-1,4-diene-3,20-dione;

4,9α,11β-trichloro-6α-difluoro-16α-methyl-17α-hydroxy-21-acetoxypregna-1,4-diene-3,20-dione; and the like.

EXAMPLE 17

This example sets forth a process for preparing 4,9α-difluoro-6α-chloro-11β,17α-dihydroxy-16α-methylpregna-1,4-diene-3,20-dione (which are substituted at the 21 position similarly to Example 11) according to the reaction sequence of Example 15 wherein $X^1$ and $X^3$ are fluoro, $X^2$ is chloro and $X^4$ is

A. 4,9α-Difluoro-6α-dichloro-11β,17α,21-trihydroxy-16α-methylpregna-1,4-diene-3,20-dione is prepared by following in principle the procedure set forth in Example 11, Part A but substituting 6α-chloro-9α-fluoro-11β,17α,21-trihydroxy-16α-methylpregna-1,4-diene-3,20-dione for flumethasone.

B. By substituting other appropriate starting materials in the process of Part A of this example other compounds of this invention are prepared such as 4,9α-difluoro-6α,21-dichloro-11β,17α-dihydroxy-16α-methylpregna-1,4-diene-3,20-dione;

4,9α-difluoro-6α-chloro-11β,17α-dihydroxy-16α-methyl-21,21-dimethoxypregna-1,4-diene-3,20-dione; and the like.

EXAMPLE 18

This example sets forth a route to the 16β-methyl steroids of this invention.

A. 4α,6-Difluoro-9α-bromo-11β-hydroxy-16β-methyl-17α,21-diacetoxypregna-1,5(6)-diene-3,20-dione A mixture of 5.0 g of 6α-fluoro-16β-methyl-17α,21-diacetoxypregna-4,9(11)-diene-3,20-dione (prepared according to British Pat. No. 1,403,962), 100 ml of dioxane and 3.5 g of 2,3-dichloro-4,6-dicyano-1,4-benzoquinone is refluxed for 10 hours. The mixture is then cooled, filtered and evaporated to dryness. The residue is dissolved in acetone and this solution is then filtered through 100 g of alumina and concentrated to yield 6α-fluoro-16β-methyl-17α,21-diacetoxypregna-1,4,9(11)-triene-3,20-dione which is further purified by recrystallization from acetone:hexane.

Ten (10) g of 6α-fluoro-16β-methyl-17α,21-diacetoxypregna-1,4,9(11)-triene-3,20-dione in 110 ml of dioxane (A.R.) plus 2.2 mls of a solution of 4.4 ml 70% HClO₄ in 200 mls of water, is treated with 4 g of dibromohydantoin in the dark at R.T. for a period of one hour or when TLC using 50% ethyl acetate/50% hexane shows the reaction to be complete. The reaction mixture is precipitated in 2 of water, stirred for 10 minutes and the crystalline precipitate collected by filtration, washed with water, and air dried to give 11.4 g of 6α-fluoro-9α-bromo-11β-hydroxy-16β-methyl-17α,21-diacetoxypregna-1,4-diene-3,20-dione.

The bromohydrin prepared in this manner (19.1 g) is mixed with 286 ml of methyl orthoformate, 96 ml of anhydrous methanol and 1.9 ml of fuming sulfuric acid and heated on a water bath at 50°–55° C. for 15 minutes. The mixture is treated with 15 ml of pyridine and poured into 300 ml of water, separated and washed three times with water. The resulting mixture is dried over anhydrous sodium sulfate, filtered and concentrated under high vacuum to a foam which is left in crushed dry ice for 16 hours to give the 11β-orthoester of 3-methoxy-6α-fluoro-9α-bromo-16β-methyl-17α,21-diacetoxypregna-1,3,5(6)-triene-20-one. The orthoester so obtained is dissolved in 300 ml of a mixture of 80% THF/20% water and treated at room temperature with a slow stream of ClO₃F until no more starting material is detected by TLC analysis. The mixture is diluted with water and the organic solvent eliminated under reduced pressure (high vacuum) at 50°–55° C. The mixture is diluted with water up to 2 liters and kept in the refrigerator for 20 hours. The resulting precipitate is filtered and dried. One (1) g of crude reaction mixture is dissolved in about 20 ml of methylene dichloride (MDC) and filtered through a 10 g column of silica with 100% MDC. The column is eluted with 1.2 liters of MDC, then with 2% ethyl acetate/98% MDC. The homgeneous fractions (containing small amounts of negative and positive polar impurities) are concentrated to dryness under high vacuum. NMR analysis of the negative polar product eluted indicates that the product is 4α,6-difluoro-9α-bromo-11β-hydroxy-16β-methyl-17α,21-diacetoxypregna-1,5(6)-diene-3,20-dione.

B. 4-fluoro-9,11-expoxy-16β-methyl-17α,21-hydroxypregna-1,4-diene-3,20-dione 21-acetate.

The resulting 9,11-bromohydrin from Part A of this example is stirred with methanol containing anhydrous potassium carbonate under nitrogen until TLC shows the reaction is complete. The reaction mixture is diluted with methanol and glacial acetic acid and concentrated under reduced pressure to a small volume. The precipitate is collected by filtration and washed with methanol and water to give 4,6α-difluoro-9,11-epoxy-16β-methyl-17α,21-dihydroxypregna-1,4-diene-3,20-dione.

The product, in turn is reacted with acetic anhydride in pyridine at room temperature for 15 hours (or until TLC shows the reaction is complete). The mixture is then poured into ice water and the solid which forms is collected by filtration, washed with water and dried to yield 4,6α-difluoro-9,11-expoxy-16β-methyl-17α,21-dihydroxypregna-1,4-diene-3,20-dione 21-acetate which is further purified through recrystallization from acetone:hexane.

Six hundred (600) mg of zinc metal dust containing 3% cupric acetate (previously blended with mortar and pestle) and 100 ml of a 1:1 mixture of dry methanol and methylene chloride are stirred together in a heat-dried nitrogen blanketed 500 ml three neck flask with septum, addition funnel, and magnetic stirrer. A solution of 2.0 g of 4,6α-difluoro-9,11-epoxy-16β-methyl-17α,21-dihydroxy-21-acetate in 120 ml of 1:1 methanol-methylene chloride solvent mixture is placed in the addition funnel and 0.6 ml of glacial acetic acid is added to the zinc slurry via syringe and stirred together for 20 minutes, after which all of the solution of the oxide is added from the addition funnel.

After 2½ hours, the reaction mixture is cooled in ice, then filtered through a cake of celite, washing thrice with the methanol-methylene chloride solvent mixture. The pH of the filtrate is adjusted to pH 7 with a solution of 1.5% potassium carbonate in methanol containing 10% water (the transient pregna-1,5-diene spontaneously rearranges to pregna-1,4-diene in neutral solution) and the methanol and methylene chloride are then evaporated while ethyl acetate is added to replace them. The ethyl acetate solution is washed three times with water, then dried over sodium sulfate and subsequently is stripped to dryness.

The residue is applied to a silica gel column prepared in 1% methanol-methylene chloride and is developed by gradient elution up to 4% methanol-methylene chloride. Recovery of material from the appropriate fractions and recrystallization from acetone-hexane affords 502 mg of 98+% pure 4-fluoro-9,11-epoxy-16β-methyl-17α,21-hydroxypregna-1,4-diene-3,20-dione 21-acetate.

C. 4,6α-Difluoro-11β,17α,21-trihydroxy-16β-methyl-pregna-1,4-diene-3,20-dione

The resulting product from Part A of this Example is mixed with a tenfold molar excess of tributyl tin hydride in tetrahydrofuran at reflux for two hours to eliminate the 9α-bromine and form 4,6α-difluoro-11β-hydroxy-16β-methyl-17α,21-diacetoxypregna-1,5(6)-diene-3,20-dione.

The resulting product is stirred with methanol containing anhydrous potassium carbonate under nitrogen at atmospheric pressure and ambient temperature until TLC shows the reaction is complete. The reaction mixture is diluted with methanol and glacial acetic acid and concentrated under reduced pressure to a small volume. The crystalline precipitate which forms is collected by filtration and washed with methanol and water to give 4,6α-difluoro-11β,17α,21-trihydroxy-16β-methylpregna-1,4-diene-3,20-dione.

EXAMPLE 19

A. 4,6α,9α-Trifluoro-11β-hydroxy-16β-methyl-17α,21-dihydroxypregna-1,4-diene-3,20-dione.

To a stirred solution of 1.8 g of 4,6α-difluoro-9,11-epoxy-16β-methyl-17α,21-dihydroxypregna-1,4-diene-3,20-dione in 30 ml of methylene chloride, cooled to 0° C. is added a cooled (−70° C.) of 2.11 g of anhydrous hydrogen fluoride in 3.7 ml of tetrahydrofuran over a period of 20 minutes. The mixture is stirred at a temperature below 10° C. for six hours and then neutralized by cautious addition of a 5% aqueous sodium bicarbonate solution. The organic layer is separated, washed with water, dried over sodium sulfate and concentrated until solid forms. The cooled mixture is then filtered and the solid dissolved in hot ethyl acetate. This solution is filtered hot and then cooled and the solid which forms is collected by filtration to yield 4,6α,9α-trifluoro-11β,17α,21-trihydroxy-16β-methylpregna-1,4-diene-3,20-dione.

B. 4,6α,9α-Trifluoro-11β-hydroxy-16β-methyl-17α,21-dihydroxypregna-1,4-diene-3,20-dione 17 alkanoates.

By following the procedure of Example 11B but substituting the compound of Part A of this Example for the corresponding steroids in Example 11B, other compounds of the 16β-methyl series of this invention are obtained such as:

4,6α,9α-trifluoro-11β,17α,21-trihydroxy-16β-methylpregna-1,4-diene-3,20-dione 17-acetate;

4,6α,9α-trifluoro-11β,17α,21-trihydroxy-16β-methylpregna-1,4-diene-3,20-dione 17-butyrate;

4,6α,9α-trifluoro-11β,17α,21-trihydroxy-16β-methylpregna-1,4-diene-3,20-dione 17-propionate;

4,6α,9α-trifluoro-11β,17α,21-trihydroxy-16β-methylpregna-1,4-diene-3,20-dione 17-valerate;

4,6α,9α-trifluoro-11β,17α,21-trihydroxy-16β-methylpregna-1,4-diene-3,20-dione 17-hexanoate; and the like.

C. 4,6α,9α-Trifluoro-11β-hydroxy-16β-methyl-17α,21-dihydroxypregna-1,4-diene-3,20-dione 17,21-dialkanoates.

By following the procedure of Example 11, Part C but substituting a compound of Part B of this example (e.g. the 17-propionate) for the corresponding steroid, other compounds of the 16β-methyl series of this invention are prepared such as:

4,6α,9α-trifluoro-11β,17α,21-trihydroxy-16β-methylpregna-1,4-diene-3,20-dione 17-propionate 21-acetate;

4,6α,9α-trifluoro-11β,17α,21-trihydroxy-16β-methylpregna-1,4-diene-3,20-dione 17,21-dipropionate;

4,6α,9α-trifluoro-11β,17α,21-trihydroxy-16β-methylpregna-1,4-diene-3,20-dione 17-propionate 21-butyrate;

4,6α,9α-trifluoro-11β,17α,21-trihydroxy-16β-methylpregna-1,4-diene-3,20-dione 17-propionate 21-valerate;

4,6α,9α-trifluoro-11β,17α,21-trihydroxy-16β-methylpregna-1,4-diene-3,20-dione 17-propionate 21-hexanoate; and the like.

D. 4,6α,9α-Trifluoro-11β-hydroxy-16β-methyl-21-halo-11β,17α-dihydroxypregna-1,4-diene-3,20-dione.

By following the procedure of Example 11D but substituting the appropriate 17-alkanoate prepared according to Part B of this example, other 16β-methyl compounds of this invention are prepared such as:

4,6α,9α-trifluoro-11β,17α-dihydroxy-16β-methyl-21-chloropregna-1,4-diene-3,20-dione 17-acetate;

4,6α,9α-trifluoro-11β,17α-dihydroxy-16β-methyl-21-chloropregna-1,4-diene-3,20-dione 17-propionate;

4,6α,9α-trifluoro-11β,17α-dihydroxy-16β-methyl-21-chloropregna-1,4-diene-3,20-dione 17-butyrate;

4,6α,9α-trifluoro-11β,17α-dihydroxy-16β-methyl-21-chloropregna-1,4-diene-3,20-dione 17-valerate;

4,6α,9α-trifluoro-11β,17α-dihydroxy-16β-methyl-21-chloropregna-1,4-diene-3,20-dione 17-hexanoate;

4,6α,9α,21-tetrafluoro-11β,17α-dihydroxy-16β-methylpregna-1,4-diene-3,20-dione 17-acetate;

4,6α,9α,21-tetrafluoro-11β,17α-dihydroxy-16β-methylpregna-1,4-diene-3,20-dione 17-butyrate;

4,6α,9α,21-tetrafluoro-11β,17α-dihydroxy-16β-methylpregna-1,4-diene-3,20-dione 17-valerate;

4,6α,9α,21-tetrafluoro-11β,17α-dihydroxy-16β-methylpregna-1,4-diene-3,20-dione 17-hexanoate; and the like.

EXAMPLE 20

A. 4,9α-difluoro-11β,17α,21-trihydroxy-16β-methylpregna-1,4-diene-3,20-dione.

4-fluoro-9,11-epoxy-16β-methyl-17α,21-hydroxypregna-1,4-diene-3,20-dione is reacted with anhydrous hydrogen fluoride according to the procedure of Part A of Example 19 to give 4,9α-difluoro-11β,17α,21-trihydroxy-16β-methylpregna-1,4-diene-3,20-dione 21-acetate. This compound in turn is treated with a small amount methanol containing anhydrous potassium carbonate under nitrogen at atmospheric pressure and ambient temperature until TLC shows that the hydrolysis of the ester is complete. The reaction mixture is diluted with methanol and glacial acetic acid and concentrated under reduced pressure to a small volume. The crystalline precipitate which forms is collected by filtration and washed with methanol and water to give 4,9α-difluoro-11β,17α,21-trihydroxy-16β-methylpregna-1,4-diene-3,20-dione.

B. 4,9α-difluoro-11β,17α,21-trihydroxy-16β-methylpregna-1,4-diene-3,20-dione 17-alkanoates.

By following in principle the procedure of Example 11B but substituting the compound prepared in Part A of this example for the steroid in Part B of Example 11, other 16β-methyl compounds of this invention are prepared such as:

4,9α-difluoro-11β,17α,21-trihydroxy-16β-methylpregna-1,4-diene-3,20-dione 17-acetate;

4,9α-difluoro-11β,17α,21-trihydroxy-16β-methylpregna-1,4-diene-3,20-dione 17-propionate;

4,9α-difluoro-11β,17α,21-trihydroxy-16β-methylpregna-1,4-diene-3,20-dione 17-butyrate;

4,9α-difluoro-11β,17α,21-trihydroxy-16β-methylpregna-1,4-diene-3,20-dione 17-valerate; and 4,9α-difluoro-11β,17α,21-trihydroxy-16β-methylpregna-1,4-diene-3,20-dione 17-hexanoate; and the like.

C. 4,9α-difluoro-11β,17α,21-trihydroxy-16β-methylpregna-1,4-diene-3,20-dione 17,21-alkanoates.

By following in principle the procedure of Example 11, Part C but substituting the appropriate 17-alkanoate from Part B of this example, other 16β-methyl compounds of this invention such as:

4,9α-difluoro-11β,17α,21-trihydroxy-16β-methylpregna-1,4-diene-3,20-dione 17-acetate 21-propionate;

4,9α-difluoro-11β,17α,21-trihydroxy-16β-methylpregna-1,4-diene-3,20-dione 17,21-dipropionate;

4,9α-difluoro-11β,17α,21-trihydroxy-16β-methylpregna-1,4-diene-3,20-dione 17-butyrate 21-propionate;

4,9α-difluoro-11β,17α,21-trihydroxy-16β-methylpregna-1,4-diene-3,20-dione 17-valerate 21propionate; and 4,9α-difluoro-11β,17α,21-trihydroxy-16β-methylpregna-1,4-diene-3,20-dione 17-hexanoate 21-propionate; and the like.

D. 4,9α-Difluoro-11β-hydroxy-16β-methyl-21-halo-11β,17α-dihydroxypregna-1,4-diene-3,20-dione.

By following in principle the procedure of Example 11D but substituting the appropriate 17-alkanoates from Part B of this Example for the steroids in Part D of Example 11, other 16β-methyl 21-halo compounds of this invention are prepared such as:

4,9α-difluoro-11β,17α-dihydroxy-16β-methyl-21-chloropregna-1,4-diene-3,20-dione 17-acetate;

4,9α-difluoro-11β,17α-dihydroxy-16β-methyl-21-chloropregna-1,4-diene-3,20-dione 17-propionate;

4,9α-difluoro-11β,17α-dihydroxy-16β-methyl-21-chloropregna-1,4-diene-3,20-dione 17-butyrate;

4,9α-difluoro-11β,17α-dihydroxy-16β-methyl-21-chloropregna-1,4-diene-3,20-dione 17-valerate;

4,9α-difluoro-11β,17α-dihydroxy-16β-methyl-21-chloropregna-1,4-diene-3,20-dione 17-hexanoate;

4,9α,21-trifluoro-11β,17α-dihydroxy-16β-methylpregna-1,4-diene-3,20-dione 17-acetate;

4,9α,21-trifluoro-11β,17α-dihydroxy-16β-methylpregna-1,4-diene-3,20-dione 17-propionate;

4,9α,21-trifluoro-11β,17α-dihydroxy-16β-methylpregna-1,4-diene-3,20-dione 17-butyrate;

4,9α,21-trifluoro-11β,17α-dihydroxy-16β-methylpregna-1,4-diene-3,20-dione 17-valerate;

4,9α,21-trifluoro-11β,17α-dihydroxy-16β-methylpregna-1,4-diene-3,20-dione 17-hexanoate; and the like.

EXAMPLE 21

A. 4-fluoro-11β,17α,21-trihydroxy-16β-methylpregna-1,4-diene-3,20-dione.

A saturated solution of hydrogen bromide in glacial acetic acid is added to 4-fluoro-9,11-epoxy-16β-methyl-17α,21-dihydroxypregna-1,4-diene-3,20-dione 21-acetate (prepared according to the process of Example 18, Part B) in acetic acid at 15° C. The mixture is allowed to stand at 15°-18° C. for five minutes and then is poured into ice water. The solid which forms is collected by filtration and dried under vacuum at 25° C. to yield 4-fluoro-9α-bromo-11β,17α,21-trihydroxy-16β-methylpregna-1,4-diene-3,20-dione 21-acetate which is recrystallized from methylene chloride:hexane. The resulting product is mixed with tributyl tin hydride and tetrahydrofuran at room temperature to eliminate the 9α-bromine and form 4-fluoro-11β,17α,21-trihydroxy-16β-methylpregna-1,4-diene-3,20-dione 21-acetate. This compound is hydrolyzed using anhydrous methanol and potassium carbonate at room temperature under a nitrogen blanket to give the 4-fluoro-11β,17α,21-trihydroxy-16β-methylpregna-1,4-diene-3,20-dione.

B. 4-fluoro-11β,17α,21-trihydroxy-16β-methylpregna-1,4-diene-3,20-dione 17-alkanoates.

By following in principle the procedure of Example 11, Part B by substituting the 11β,17α,21-trihydroxy compound of Part B of this example for the corresponding steroid in Example 11, Part B, other 16β-methyl compounds of this invention are prepared such as:

4-fluoro-11β,17α,21-trihydroxy-16β-methylpregna-1,4-diene-3,20-dione 17-acetate;

4-fluoro-11β,17α,21-trihydroxy-16β-methylpregna-1,4-diene-3,20-dione 17-propionate;

4-fluoro-11β,17α,21-trihydroxy-16β-methylpregna-1,4-diene-3,20-dione 17-butyrate;

4-fluoro-11β,17α,21-trihydroxy-16β-methylpregna-1,4-diene-3,20-dione 17-valerate; and 4-fluoro-11β,17α,21-trihydroxy-16β-methylpregna-1,4-diene-3,20-dione 17-hexanoate; and the like.

C. 4-fluoro-11β,17α,21-trihydroxy-16β-methylpregna-1,4-diene-3,20-dione 17,21-dialkanoates.

By following in principle the procedure of Example 11, Part C but substituting the appropriate 17-alkanoate from Part B of this example, other 17β-methyl compounds of this invention such as:

4-fluoro-11β,17α,21-trihydroxy-16β-methylpregna-1,4-diene-3,20-dione 17-acetate 21-propionate;

4-fluoro-11β,17α,21-trihydroxy-16β-methylpregna-1,4-diene-3,20-dione 17,21-dipropionate;

4-fluoro-11β,17α,21-trihydroxy-16β-methylpregna-1,4-diene-3,20-dione 17-butyrate 21-propionate;

4-fluoro-11β,17α,21-trihydroxy-16β-methylpregna-1,4-diene-3,20-dione 17-valerate 21-propionate; and 4-fluoro-11β,17α,21-trihydroxy-16β-methylpregna-1,4-diene-3,20-dione 17hexanoate 21-propionate; and the like.

D. 4-fluoro-11β-hydroxy-16β-methyl-21-halo-11β,17α-dihydroxypregna-1,4-diene-3,20-dione.

By following in principle the procedure of Example 11D but substituting the appropriate 17-alkanoates from Part B of this Example for the steroids in Part D of Example 11, other 16β-methyl compounds of this invention are prepared such as:

4-fluoro-11β,17α-dihydroxy-16β-methyl-21-chloropregna-1,4-diene-3,20-dione 17-acetate;

4-fluoro-11β,17α-dihydroxy-16β-methyl-21-chloropregna-1,4-diene-3,20-dione 17-propionate;

4-fluoro-11β,17α-dihydroxy-16β-methyl-21-chloropregna-1,4-diene-3,20-dione 17-butyrate;

4-fluoro-11β,17α-dihydroxy-16β-methyl-21-chloropregna-1,4-diene-3,20-dione 17-valerate;

4-fluoro-11β,17α-dihydroxy-16β-methyl-21-chloropregna-1,4-diene-3,20-dione 17-hexanoate;

4,21-difluoro-11β,17α-dihydroxy-16β-methylpregna-1,4-diene-3,20-dione 17-acetate;

4,21-difluoro-11β,17α-dihydroxy-16β-methylpregna-1,4-diene-3,20-dione 17-propionate;

4,21-difluoro-11β,17α-dihydroxy-16β-methylpregna-1,4-diene-3,20-dione 17-butyrate;

4,21-difluoro-11β,17α-dihydroxy-16β-methylpregna-1,4-diene-3,20-dione 17-valerate;

4,21-difluoro-11β,17α-dihydroxy-16β-methylpregna-1,4-diene-3,20-dione 17-hexanoate; and the like.

EXAMPLE 22

A. 4,6α-difluoro-11β,17α,21-trihydroxy-16β-methylpregna-1,4-diene-3,20-dione 17-alkanoates.

By following in principle the procedure of Example 11B but substituting the compound prepared in Part C of Example 18 for the steroid in Part B of Example 11, other 16β-methyl compounds of this invention are prepared such as:

4,6α-difluoro-11β,17α,21-trihydroxy-16β-methylpregna-1,4-diene-3,20-dione 17-acetate;

4,6α-difluoro-11β,17α,21-trihydroxy-16β-methylpregna-1,4-diene-3,20-dione 17-propionate;

4,6α-difluoro-11β,17α,21-trihydroxy-16β-methylpregna-1,4-diene-3,20-dione 17-butyrate;

4,6α-difluoro-11β,17α,21-trihydroxy-16β-methylpregna-1,4-diene-3,20-dione 17-valerate; and 4,6α-difluoro-11β,17α,21-trihydroxy-16β-methylpregna-1,4-diene-3,20-dione 17-hexanoate; and the like.

B. 4,6α-difluoro-11β,17α,21-trihydroxy-16β-methylpregna-1,4-diene-3,20-dione 17,21-alkanoates.

By following in principle the procedure of Example 11, Part C but substituting the appropriate 17-alkanoate from Part B of this example, other 17β-methyl compounds of this invention such as:

4,6α-difluoro-11β,17α,21-trihydroxy-16β-methylpregna-1,4-diene-3,20-dione 17-acetate 21-propionate;

4,6α-difluoro-11β,17α,21-trihydroxy-16β-methylpregna-1,4-diene-3,20-dione 17,21-dipropionate;

4,6α-difluoro-11β,17α,21-trihydroxy-16β-methylpregna-1,4-diene-3,20-dione 17-butyrate 21-propionate;

p 4,6α-difluoro-11β,17α,21-trihydroxy-16β-methylpregna-1,4-diene-3,20-dione 17-valerate 21-propionate; and 4,6α-difluoro-11β,17α,21-trihydroxy-16β-methylpregna-1,4-diene-3,20-dione 17-hexanoate 21-propionate; and the like.

D. 4,6α-Difluoro-11β-hydroxy-16β-methyl-21-halo-11β,17α-dihydroxypregna-1,4-diene-3,20-dione.

By following in principle the procedure of Example 11D but substituting the appropriate 17-alkanoates of this Example from Part B for the steroids in Part D of Example 11, other 16β-methyl compounds of this invention are prepared such as:

4,6α-difluoro-11β,17α-dihydroxy-16β-methyl-21-chloropregna-1,4-diene-3,20-dione 17-acetate;

4,6α-difluoro-11β,17α-dihydroxy-16β-methyl-21-chloropregna-1,4-diene-3,20-dione 17-propionate;

4,6α-difluoro-11β,17α-dihydroxy-16β-methyl-21-chloropregna-1,4-diene-3,20-dione 17-butyrate;

4,6α-difluoro-11β,17α-dihydroxy-16β-methyl-21-chloropregna-1,4-diene-3,20-dione 17-valerate;

4,6α-difluoro-11β,17α-dihydroxy-16β-methyl-21-chloropregna-1,4-diene-3,20-dione 17-hexanoate;

4,6α,21-trifluoro-11β,17α-dihydroxy-16β-methylpregna-1,4-diene-3,20-dione 17-acetate;

4,6α,21-trifluoro-11β,17α-dihydroxy-16β-methylpregna-1,4-diene-3,20-dione 17-propionate;

4,6α,21-trifluoro-11β,17α-dihydroxy-16β-methylpregna-1,4-diene-3,20-dione 17-butyrate;

4,6α,21-trifluoro-11β,17α-dihydroxy-16β-methylpregna-1,4-diene-3,20-dione 17-valerate;

4,6α,21-trifluoro-11β,17α-dihydroxy-16β-methylpregna-1,4-diene-3,20-dione 17-hexanoate; and the like.

EXAMPLE 23

A. 4-fluoro-9α-chloro-11β,17α,21-trihydroxy-16β-methylpregna-1,4-diene-3,20-dione To a stirred solution of 4-fluoro-9,11-epoxy-16β-methyl-17α,21-dihydroxypregna-1,4-diene-3,20-dione 21acetate (prepared as in Example 18B) in anhydrous chloroform, are added over a perid of 35 minutes and at 0° C., a 0.45 normal chloroform solution of dry hydrogen chloride. The mixture is stirred for one hour at 0° C. and then diluted with water. The organic layer is separated, washed with aqueous sodium bicarbonate solution and with water, dried over sodium sulfate and evaporated under reduced pressure to yield 4-fluoro-9α-chloro-11β,17α,21-trihydroxy-16β-methylpregna-1,4-diene-3,20-dione 21-acetate which is recrystallized from acetone:hexane. The acetate is hydrolized using potassium carbonate in methanol under nitrogen to form 4-fluoro-9α-chloro-11β,17α,21-trihydroxy-16β-methylpregna-1,4-diene-3,20-dione.

B. 4-fluoro-9α-chloro-11β,17α,21-trihydroxy-16β-methylpregna-1,4-diene-3,20-dione 17-alkanoate.

By following in principle the procedure of Example 11, Part B but substituting the compound of Part A of this example for the steroid used in Example 11, Part B, other 16β-methyl compounds of this invention are prepared such as:

4-fluoro-9α-chloro-11β,17α,21-trihydroxy-16β-methylpregna-1,4-diene-3,20-dione 17-acetate;

4-fluoro-9α-chloro-11β,17α,21-trihydroxy-16β-methylpregna-1,4-diene-3,20-dione 17-propionate;

4-fluoro-9α-chloro-11β,17α,21-trihydroxy-16β-methylpregna-1,4-diene-3,20-dione 17-butyrate;

4-fluoro-9α-chloro-11β,17α,21-trihydroxy-16β-methylpregna-1,4-diene-3,20-dione 17-valerate; and 4-fluoro-9α-chloro-11β,17α,21-trihydroxy-16β-methylpregna-1,4-diene-3,20-dione 17-hexanoate; and the like.

C. 4-fluoro-9α-chloro-11β,17α,21-trihydroxy-16β-methylpregna-1,4-diene-3,20-dione 17,21-alkanoates.

By following in principle the procedure of Example 11, Part C but substituting the appropriate 17-alkanoate from Part B of this example, other 17β-methyl compounds of this invention such as:

4-fluoro-9α-chloro-11β,17α,21-trihydroxy-16β-methylpregna-1,4-diene-3,20-dione 17-acetate 21-propionate;

4-fluoro-9α-chloro-11β,17α,21-trihydroxy-16β-methylpregna-1,4-diene-3,20-dione 17,21-dipropionate;

4-fluoro-9α-chloro-11β,17α,21-trihydroxy-16β-methylpregna-1,4-diene-3,20-dione 17-butyrate 21-propionate;

4-fluoro-9α-chloro-11β,17α,21-trihydroxy-16β-methylpregna-1,4-diene-3,20-dione 17-valerate 21-propionate; and 4-fluoro-9α-chloro-11β,17α,21-trihydroxy-16β-methylpregna-1,4-diene-3,20-dione 17-hexanoate 21-propionate; and the like.

D. 4-fluoro-9α-chloro-11β-hydroxy-16β-methyl-21-halo-11β,17α-dihydroxypregna-1,4-diene-3,20-dione.

By following in principle the procedure of Example 11D but substituting the appropriate 17-alkanoates of this Example from Part B for the steroids in Part D of Example 11, other 16β-methyl compounds of this invention are prepared such as:

4-fluoro-9α,21-dichloro-11β,17α-dihydroxy-16β-methylpregna-1,4-diene-3,20-dione 17-acetate;

4-fluoro-9α,21-dichloro-11β,17α-dihydroxy-16β-methylpregna-1,4-diene-3,20-dione 17propionate;

4-fluoro-9α,21-dichloro-11β,17α-dihydroxy-16β-methylpregna-1,4-diene-3,20-dione-17-butyrate;

4-fluoro-9α,21-dichloro-11β,17α-dihydroxy-16β-methylpregna-1,4-diene-3,20-dione 17-valerate;

4-fluoro-9α,21-dichloro-11β,17α-dihydroxy-16β-methylpregna-1,4-diene-3,20-dione 17-hexanoate;

4,21-difluoro-9α-chloro-11β,17α-dihydroxy-16β-methylpregna-1,4-diene-3,20-dione 17-acetate;

4,21-difluoro-9α-chloro-11β,17α-dihydroxy-16β-methylpregna-1,4-diene-3,20-dione 17-propionate;

4,21-difluoro-9α-chloro-11β,17α-dihydroxy-16β-methylpregna-1,4-diene-3,20-dione 17-butyrate;

4,21-difluoro-9α-chloro-11β,17α-dihydroxy-16β-methylpregna-1,4-diene-3,20-dione 17-valerate;

4,21-difluoro-9α-chloro-11β,17α-dihydroxy-16β-methylpregna-1,4-diene-3,20-dione 17-hexanoate; and the like.

EXAMPLE 24

This example sets forth a process for preparing the 21,21-dihydroxy compounds of this invention from the corresponding 21-monohydroxy compound prepared according to the appropriate portions of Examples 1–23.

A solution of 0.68 g of cupric acetate hydrate in 40 ml methanol is added to a slurry of 12.0 g of 4,6α,9α-trifluoro-11β,21-dihydroxy-16α,17α-isopropylidenedioxypregna-1,4-diene-3,20-dione is 130 ml of dry methanol. Air is then sparged through the mixture for 2 hours. Thereafter, the mixture is evaporated to dryness and the residue is taken up in ethyl acetate and washed with water and then with a dilute aqueous solution of potassium bicarbonate and then again with water. The solution is evaporated to dryness and the resulting residue is then dissolved in acetone. The acetone solution is diluted wih a substantial volume of water whereupon the resulting precipitate is filtered and dried under vacuum to yield 4,6',9α-trifluoro-11β,21,21-trihydroxy-16α,1-7α-isopropylidenedioxypregna-1,4-diene-3,20-dione.

Similarly, by following in principle the procedure of this Example but substituting other appropriate starting materials for 4,6α,9α-trifluoro-11β,21-trihydroxy-16α,17α-isopropylidenedioxypregna-1,4-diene-3,20-dione the following compounds are prepared:

4,6α-difluoro-9α,11β-dichloro-21,21-dihydroxy-16α,17α-isopropylidenedioxypregna-1,4-diene-3,20-dione;

4-chloro-6α,9α-difluoro-11β,21,21-trihydroxy-16α,1-7α-isopropylidenedioxypregna-1,4-diene-3,20-dione;

4α-fluoro-11β,21,21-trihydroxy-16α,17α-isopropylidenedioxypregna-1,4-diene-3,20-dione 4,9α-difluoro-11β,21,21-dihydroxy-16α,17α-isopropylidenedioxypregna-1,4-diene-3,20-dione;

4-fluoro-6α,9α,11β-trichloro-21,21-dihydroxy-16α,1-7α-isopropylidenedioxypregna-1,4-diene-3,20-dione;

4,6α,9α-trifluoro-11β,17α,21,21-tetrahydroxy-16β-methylpregna-1,4-diene-3,20-dione;

4-chloro-6α,9α-difluoro-11β,17α-21,21-tetrahydroxy-16β-methylpregna-1,4-diene-3,20-dione;

4,6α,9β-trifluoro-11β,17α,21,21-tetrahydroxy-16α-methylpregna-1,4-diene-3,20-dione;

4,9α-difloro-11β,17α,21,21-tetrahydroxy-16α-methylpregna-1,4-diene-3,20-dione; and the like.

EXAMPLE 25

This example sets forth a process for making the following Δ⁴ steroids of this invention.

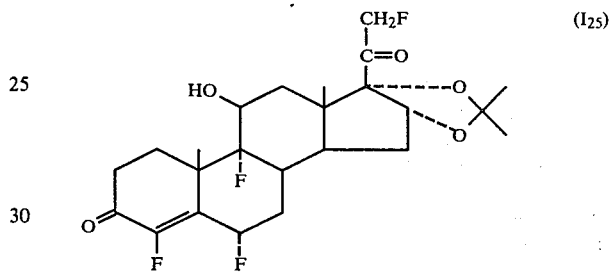

A solution of 25 mg of tris-(triphenylphosphine) chlorohodium in 6 ml of benzene and 15 ml of ethanol is stirred under hydrogen for 60 minutes. 4,6α,9α,21-tetrafluoro-11β-hydroxy-16α,17α-isopropylidenedioxypregna-1,4-diene-3,20-dione (244 mg) represented by Formula ($I_{25}$), is added and the resulting solution is stirred under hydrogen at room temperature at atmospheric pressure. After hydrogen uptake is complete, the solution is evaporated to dryness and the residue taken up in a mixture of petroleum ether and methylene chloride. The pure product is isolated by column chromatography on silica gel to give 4,6α,9α,21-tetrafluoro-11β-hydroxy-16α,17α-isopropylidenedioxypregn-4-ene-3,20-dione.

Similarly, by substituting other Δ¹,⁴ steroids of this invention made according to Examples 1–24 for the compound of formula ($I_{25}$), other corresponding Δ⁴ steroids are prepared such as 4,6α,9α-trifluoro-11β-hydroxy-16α-methyl-17α-propionyloxy-21-acetoxypregn-4-ene-3,20-dione, and the like.

EXAMPLE 26

This example sets forth a process for preparing an 11-keto compound of this invention by oxidizing any of the 11β-hydroxy steroids set forth in Examples 1–24.

One g of 4,6α,9α,21-tetrafluoro-11β-hydroxy-16α,1-7α-isopropylidenedioxypregna-1,4-diene-3,20-dione is dissolved in 50 ml of acetone and treated at room temperature with Jones reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely 4,6α,9α,21- tetrafluoro-16α,17α-isopropylidenedioxypregna-1,4-diene-3,11,20-trione.

EXAMPLE 27

This example sets forth a process for converting a $\Delta^4$-steroid to a $\Delta^{1,4}$ steroid.

A mixture of 0.5 g of 4,6α-difluoro-11β,21-dihydroxy-16α,17α-isopropylidenedioxypregn-4-ene-3,20-dione, 10 ml of dioxane and 0.35 g. of 2,3-dichloro-5,6-dicyano-1,4-benzoquinone is refluxed for 10 hours. The mixture is then cooled, filtered and evaporated to dryness. The residue is dissolved in acetone and this solution is then filtered through 10 g of alumina and concentrated to yield 4,6α-difluoro-11β,21-dihydroxy-16α,17α-isopropylidenedioxypregna-1,4-diene-3,20-dione which is further purified by recrystallization from acetone:hexane.

EXAMPLE 28

Formulation

In this example a formulation is prepared of the following composition

|  | % w/w |
|---|---|
| 4,6α,9α-trifluoro-11β-hydroxy-16α,17α-isopropylidenedioxypregna-1,4-diene-3,20-dione | 0.025 |
| Stearyl Alcohol | 30.0 |
| PEG 6000 | 5.0 |
| 1,2,6-Hexanetriol | 2.5 |
| Citric Acid Anhydrous, USP | 0.02 |
| Propylene Glycol, USP, q.s. | 100.0 |

The steroid is dissolved in 624.8 grams of propylene glcyol at 90°–95° C. The latter is then mixed with the other ingredients at 80°–85° C. to give the desired formulation.

EXAMPLE 29

Biological Activity

Anti-inflammatory Activity

This example sets forth a method for determining the topical anti-inflammatory activity of compounds of this invention. The topical anti-inflammatory activity potential for each compound was assayed using a modified Stoughton/McKenzie vaso-constriction assay in humans, i.e., McKenzie, W. W. and Stoughton, R. B. "Method for Comparing Percutaneous Absorption of Steroids" *Arch. Dermat.* 86, 608 (1962).

Eight normal adult human subjects are treated on four sites on each forearm by topical administration with alcoholic solutions containing $1 \times 10^{-5}$ and $1 \times 10^{-6}$ g/ml of each of the compounds to provide 64 total test sites for each compound in a series (32 for each concentration). Areas of the subjects' forearms are outlined by a rubber stamp grid coated with silicone grease, and 10 microliters of each solution were applied per $7 \times 7$ mm square site. After the preparations dried, the areas on each forearm are covered with Saran ® wrap and the margins sealed with tape. The occlusive wrap is removed after 18 hours. Twenty-four hours after application, the presence or absence of vasoconstriction is noted by visual examination by two independent observers, and expressed as the number of sites responding (vasoconstriction) and is calculated as a percentage of the total number of sites. Also, the intensity of the vasoconstriction is scored on a 0, 1, 2 scale, 2 being the most intense reaction. Both scores are used in constructing dose-response graphs according to methods set forth in an article by Place, V. A. et al. entitled "Precise Evaluation of Topically Applied Corticosteroid Potency", Arch Derm, 101, 531–537 (1970). The activity is determined relative to fluocinolone acetonide (FA). Generally, if the compound exhibits activity in the range of 0.1 times the activity of FA, it is an active compound.

Thymolytic Activity

The compounds to be tested, including a hydrocortisone standard, are prepared in three or more concentrations by suspension in a sodium carboxymethylcellulose vehicle. Animals receive the test materials by subcutaneous injection of 0.5 ml of the suspension on each of three successive days. Four hours following the final injection, the rats are sacrificed and the thymus gland of each animal removed and weighed and a determination of activity relative to hydrocortisone (HC) obtained. HC has low thymolytic activity.

Generally, the compounds of this invention show high anti-inflammatory activity but low thymolytic activity, thus exhibiting a therapeutic advantage over compounds of the art.

I claim as my Invention:

1. A compound chosen from those represented by the formula

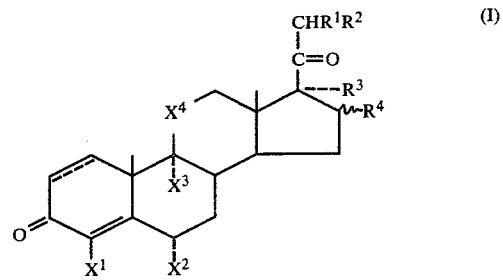

(I)

wherein
X$^1$ is fluoro or chloro;
X$^2$ is hydrogen, fluoro or chloro;
X$^3$ is hydrogen, fluoro, chloro or bromo;
X$^4$ is =C=O or

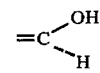

or may be

when X$^3$ is chloro;
R$^1$ is hydrogen, fluoro, chloro, bromo, hydroxy or methoxy;
R$^2$ is fluoro, chloro, bromo, hydroxy or alkanoyloxy of 2 through 6 carbon atoms when R$^1$ is hydrogen or R$^2$ is the same as R$^1$ when R$^1$ is fluoro, chloro, hydroxy or methoxy;
R$^3$ is alkanoyloxy of 2 through 6 carbon atoms when R$^4$ is α-methyl or β-methyl or R$^3$ and R$^4$ together are

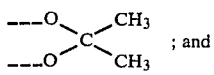 ; and the solid and broken lines between the 1- and 2-positions in the A ring of the steroid nucleus represents a single or a double bond when $R^3$ and $R^4$ together are

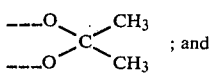 ; and and a double bond when $R^3$ is alkanoyloxy and $R^4$ is α-methyl or β-methyl.

2. The compound of claim 1 wherein $X^1$ is fluoro or chloro, $X^2$ is hydrogen or fluoro, $X^3$ is hydrogen or fluoro; $X^4$ is

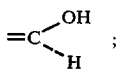 ;

$R^1$ is hydrogen, hydroxy or methoxy; $R^2$ is hydroxy; fluoro, chloro or alkanoyloxy of two to six carbon atoms when $R^1$ is hydrogen or $R^2$ is the same as $R^1$ when $R^1$ is hydroxy or methoxy; and $R^3$ and $R^4$ together are 16α,17α-isopropylidenedioxy.

3. The compound of claim 2 wherein $X^1$, $X^2$ and $X^3$ are each fluoro; $X^4$ is

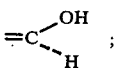 ;

$R^1$ is hydrogen, $R^2$ is hydroxy, and there is a double bond between C-1 and C-2, namely 4,6α,9α-trifluoro-11β,21-dihydroxy-16α,17α-isopropylidenedioxypregna-1,4-diene-3,20-dione.

4. The compound of claim 2 wherein $X^1$, $X^2$ and $X^3$ are each fluoro; $X^4$ is

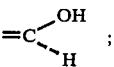 ;

$R^1$ is hydrogen, $R^2$ is propionyloxy and there is a double bond between C-1 and C-2, namely 4,6α,9α-trifluoro-11β-hydroxy-16α,17α-isopropylidenedioxy-21-propionyloxypregna-1,4-diene-3,20-dione.

5. The compound of claim 2 wherein $R^2$, $X^1$, $X^2$ and $X^3$ are each fluoro; $X^4$ is

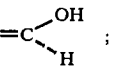 ;

$R^1$ is hydrogen, and there is a double bond between C-1 and C-2, namely 4,6α,9α,21-tetrafluoro-11β-hydroxy-16α,17α-isopropylidenedioxy-21-propionyloxypregna-1,4-diene-3,20-dione.

6. The compound of claim 2 wherein $X^1$ and $X^2$ are each fluoro; $X^4$ is

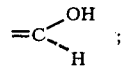 ;

$R^1$ is hydrogen, $R^2$ is fluoro; and there is a double bond between C-1 and C-2, namely 4,6α,21-trifluoro-11β-hydroxy-16α,17α-isopropylidenedioxy-21-propionyloxypregna-1,4-diene-3,20-dione.

7. The compound of claim 2 wherein $X^1$, $X^2$ and $X^3$ are each fluoro; $X^4$ is

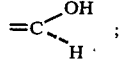 ;

$R^1$ is hydrogen; $R^2$ is chloro; and there is a double bond between C-1 and C-2, namely 4,6α,9α-trifluoro-11β-hydroxy-16α,17α-isopropylidenedioxy-21-propionyloxypregna-1,4-diene-3,20-dione.

8. The compound of claim 2 wherein $X^1$, $X^2$ are each fluoro; $X^3$, $X^4$ and $R^2$ are all chloro; $R^1$ is hydrogen, and there is a double bond between C-1 and C-2, namely 4,6α-difluoro-9α,11β,21-trichloro-16α,17α-isopropylidenedioxypregna-1,4-diene-3,20-dione.

9. The compound of claim 2 wherein $X^1$ and $X^2$ are both fluoro; $X^3$ is hydrogen or fluoro; $X^4$ is

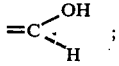 ;

$R^1$ and $R^2$ are both the same and are chosen from the group consisting of hydroxy and methoxy, and $R^3$ and $R^4$ together are 16α,17α-isopropylidenedioxy.

10. The compound of claim 9 wherein $X^3$ is fluoro, $X^4$ is

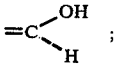 , $R^1$ and $R^2$ are both methoxy; and there is a double bond between the C-1 and C-2, namely 4,6α,9α-trifluoro-11β-hydroxy-16α,17α-isopropylidenedioxy-21,21-dimethoxypregna-1,4-diene-3,20-dione.

11. The compound of claim 1 wherein $X^1$, $X^3$ and $R^2$ are chloro, $X^2$ is fluoro; $X^4$ is

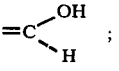 ;

$R^3$ and $R^4$ together are 16,17α-isopropylidenedioxy; and there is a double bond between C-1 and C-2, namely 4,9α,11β,21-tetrachloro-6α-fluoro-16α,17α-isopropylidenedioxypregna-1,4-diene-3,20-dione.

12. The compound of claim 1 wherein $X^1$ is chloro; $X^2$, $X^3$ and $R^2$ are each fluoro; $X^4$ is

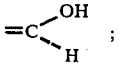 ;

$R^1$ is hydrogen; $R^3$ and $R^4$ together are isopropylidenedioxy; and there is a double bond between C-1 and C-2, namely 4-chloro-6α,9α,21-trifluoro-11β-hydroxy- 16α,17α-isopropylidenedioxypregna-1,4-diene-3,20-dione.

13. The compound of claim 1 wherein $X^1$ is chloro; $X^2$ and $X^3$ are each fluoro; $X^4$ is

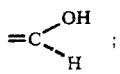

$R^1$ is hydrogen, $R^2$ is hydroxy; $R^3$ and $R^4$ together are isopropylidenedioxy; and there is a double bond between C-1 and C-2, namely 4-chloro-6α,9α-difluoro-11β,21-dihydroxy-16α,17α-isopropylidenedioxypregna-1,4-diene-3,20-dione.

14. The compound of claim 1 wherein $X^1$ is chloro; $X^2$ and $X^3$ are each fluoro; $X^4$ is

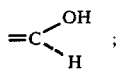

$R^1$ is hydrogen, $R^2$ is acetoxy; $R^3$ and $R^4$ together are isopropylidenedioxy and there is a double bond between C-1 and C-2, namely 4-chloro-6α,9α-difluoro,11β-hydroxy-16α,17α-isopropylidenedioxy-21-acetoxypregna-1,4-diene-3,20-dione.

15. The compound of claim 1 wherein $X^1$ is fluoro or chloro; $X^2$ is hydrogen or fluoro; $X^3$ is fluoro, chloro or hydrogen; $X^4$ is

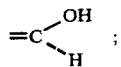

$R^1$ is hydrogen, hydroxy or methoxy; $R^2$ is fluoro, chloro, hydroxy, methoxy or alkanoyloxy of two to six carbon atoms when $R^1$ is hydrogen or $R^2$ is the same as $R^1$ when $R^1$ is hydroxy or methoxy; $R^3$ is hydroxy or alkanoyloxy of 2–6 carbon atoms; $R^4$ is α-methyl or β-methyl; and there is a double bond between C-1 and C-2 of the steroid ring.

16. The compound of claim 15 wherein $R^4$ is β-methyl.

17. The compound of claim 16 wherein $X^1$ is fluoro; $X^2$ is fluoro or hydrogen; $X^3$ is fluoro, chloro or hydrogen; $X^4$ is

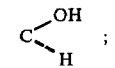

$R^1$ is hydrogen or methoxy; $R^2$ is methoxy when $R^1$ is methoxy or $R^2$ is hydroxy, alkanoyloxy of two to six carbon atoms or chloro when $R^1$ is hydrogen; and $R^3$ is hydroxy or alkanoyloxy of two to six carbon atoms.

18. The compound of claim 17 wherein $X^1$, $X^2$ and $X^3$ are each fluoro, $R^1$ is hydrogen and $R^3$ is alkanoyloxy of three to five carbon atoms.

19. The compound of claim 18 wherein $R^2$ is chloro and $R^3$ is propionyloxy, namely 4,6α,9α-trifluoro-11β-hydroxy-16β-methyl-17α-propionyloxy-21-chloropregna-1,4-diene-3,20-dione.

20. The compound of claim 18 wherein $R^2$ is chloro and $R^3$ is butyryloxy, namely 4,6α,9α-trifluoro-11β-hydroxy-16β-methyl-17α-butyryloxy-21-chloropregna-1,4-diene-3,20-dione.

21. The compound of claim 18 wherein $R^2$ is hydroxy and $R^3$ is butyryloxy, namely 4,6α,9α-trifluoro-11β,21-dihydroxy-16β-methyl-17α-butyryloxypregna-1,4-diene-3,20-dione.

22. The compound of claim 18 wherein $R^2$ is hydroxy and $R^3$ is valeryloxy, namely 4,6α,9α-trifluoro-11β,21-dihydroxy-16β-methyl-17α-valeryloxypregna-1,4-diene-3,20-dione.

23. The compound of claim 17 wherein $X^1$ and $X^3$ are both fluoro, $X^2$ is hydrogen, $R^1$ is hydrogen, and $R^3$ is alkanoyloxy of three to five carbon atoms.

24. The compound of claim 23 wherein $R^2$ is chloro and $R^3$ is propionyloxy, namely 4,9α-difluoro-11β-hydroxy-16β-methyl-17α-propionyloxy-21-chloropregna-1,4-diene-3,20-dione.

25. The compound of claim 23 wherein $R^3$ is chloro and $R^3$ is butyryloxy, namely 4,9α-difluoro-11β-hydroxy-16β-methyl-17α-butyryloxy-21-chloropregna-1,4-diene-3,20-dione.

26. The compound of claim 23 wherein $R^2$ is hydroxy and $R^3$ is butyryloxy, namely 4,9α-difluoro-11β,21-dihydroxy-16β-methyl-17α-butyryloxypregna-1,4-diene-3,20-dione.

27. The compound of claim 23 wherein $R^2$ is hydroxy and $R^3$ is valeroyloxy namely 4,9α-difluoro-11β,21-dihydroxy-16β-methyl-17α-valeryloxypregna-1,4-diene-3,20-dione.

28. The compound of claim 17 wherein $X^1$ and $X^2$ are both fluoro, $X^3$ is hydrogen, $X^4$ is hydroxy, $R^1$ is hydrogen, $R^3$ is alkanoyloxy of three to five carbon atoms.

29. The compound of claim 28 wherein $R^2$ is chloro, and $R^3$ is propionyloxy, namely 4,6α-difluoro-11β-hydroxy-16β-methyl-17α-propionyloxy-21-chloropregna-1,4-diene-3,20-dione.

30. The compound of claim 28 wherein $R^2$ is chloro and $R^3$ is butyryloxy, namely 4,6α-difluoro-11β-hydroxy-16β-methyl-17α-butyryloxy-21-chloropregna-1,4-diene-3,20-dione.

31. The compound of claim 28 wherein $R^2$ is hydroxy, $R^3$ is butyryloxy, namely 4,6α-difluoro-11β,21-dihydroxy-16β-methyl-17α-butyryloxy-pregna-1,4-diene-3,20-dione.

32. The compound of claim 28 wherein $R^2$ is hydroxy, $R^3$ is valeryloxy, namely 4,6α-difluoro-11β,21-dihydroxy-16β-methyl-17α-valeryloxy-pregna-1,4-diene-3,20-dione.

33. The compound of claim 17 wherein $X^1$ is fluoro, $X^2$ is hydrogen, $X^3$ is α-chloro, $X^4$ is hydroxy, $R^1$ is hydrogen, $R^2$ and $R^3$ are both propionyloxy, namely 4-fluoro,9α-chloro-11β-hydroxy-16β-methyl-17α,21-dipropionyloxypregna-1,4-diene-3,20-dione.

34. The compound of claim 17 wherein $X^1$, $X^2$ and $X^3$ are each fluoro, $X^4$ is hydroxy, $R^1$ is hydrogen and $R^2$ and $R^3$ are both propionyloxy, namely 4,6α,9α-trifluoro-11β-hydroxy-16β-methyl-17α,21-dipropionyloxypregna-1,4-diene-3,20-dione.

35. The compound of claim 15 wherein $R^4$ is α-methyl.

36. The compound of claim 35 wherein $X^1$ is fluoro; $X^2$ is fluoro or hydrogen; $X^3$ is fluoro, chloro or hydrogen; $X^4$ is

$R^1$ is hydrogen, hydroxy or methoxy; $R^2$ is the same as $R^1$ when $R^1$ is hydroxy or methoxy or $R^2$ is hydroxy, alkanoyloxy of two to six carbon atoms, chloro or fluoro when $R^1$ is hydrogen; and $R^3$ is hydroxy or alkanoyloxy of two to six carbon atoms.

37. The compound of claim 36 wherein $X^1$, $X^2$ and $X^3$ are each fluoro, $R^1$ is hydrogen and $R^3$ is alkanyoyloxy of three to five carbon atoms.

38. The compound of claim 37 wherein $R^2$ is chloro and $R^3$ is propionyloxy, namely 4,6α,9α-trifluoro-11β-hydroxy-16α-methyl-17α-propionyloxy-21-chloropregna-1,4-diene-3,20-dione.

39. The compound of claim 37 wherein $R^2$ is chloro and $R^3$ is butyryloxy, namely 4,6α,9α-trifluoro-11β-hydroxy-16α-methyl-17α-butyryloxy-21-chloro-pregna-1,4-diene-3,20-dione.

40. The compound of claim 37 wherein $R^2$ is hydroxy and $R^3$ is valeryloxy, namely 4,6α,9α-trifluoro-11β,21α-dihydroxy-16α-methyl-17α-valeryloxypregna-1,4-diene-3,20-dione.

41. The compound of claim 37 wherein $R^2$ is hydroxy and $R^3$ is butyryloxy, namely 4,6α,9α-trifluoro-11β,21α-dihydroxy-16α-methyl-17α-butyryloxypregna-1,4-diene-3,20-dione.

42. The compound of claim 36 wherein $X^1$ and $X^3$ are both fluoro, $X^2$ is hydrogen, $R^1$ is hydrogen and $R^3$ is alkanoyloxy of three to five carbon atoms.

43. The compound of claim 42 wherein $R^2$ is chloro and $R^3$ is propionyloxy, namely 4,9α-difluoro-11β-hydroxy-16α-methyl-17α-propionyloxy-21-chloropregna-1,4-diene-3,20-dione.

44. The compound of claim 42 wherein $R^2$ is chloro and $R^3$ is butyryloxy, namely 4,9α-difluoro-11β-hydroxy-16α-methyl-17α-butyryloxy-21-chloropregna-1,4-diene-3,20-dione.

45. The compound of claim 42 wherein $R^2$ is hydroxy and $R^3$ is butyryloxy namely 4,9α-difluoro-11β,21-dihydroxy-16α-methyl-17α-butyryloxypregna-1,4-diene-3,20-dione.

46. The compound of claim 42 wherein $R^2$ is hydroxy and $R^3$ is valeroyloxy namely 4,9α-difluoro-11β,21-dihydroxy-16α-methyl-17α-valeryloxypregna-1,4-diene-3,20-dione.

47. The compound of claim 36 wherein $X^1$ and $X^2$ are both fluoro, $X^3$ is hydrogen, $X^4$ is hydroxy, $R^1$ is hydrogen, $R^3$ is alkanoyloxy of three to five carbon atoms.

48. The compound of claim 47 wherein $R^2$ is chloro and $R^3$ is propionyloxy namely, 4,6α-difluoro-11β-hydroxy-16α-methyl-17α-propionyloxy-21-chloropregna-1,4-diene-3,20-dione.

49. The compound of claim 47 wherein $R^2$ is chloro and $R^3$ is butyryloxy, namely 4,6α-difluoro-11β-hydroxy-16α-methyl-17α-butyryloxy-21-chloropregna-1,4-diene-3,20-dione.

50. The compound of claim 46 wherein $R^2$ is hydroxy and $R^3$ is butyryloxy, namely 4,6α-difluoro-11β,21-dihydroxy-16α-methyl-17α-butyryloxypregna-1,4-diene-3,20-dione.

51. The compound of claim 36 wherein $X^1$, $X^2$ and $X^3$ are each fluoro; $X^4$ is hydroxy, $R^1$ is hydrogen, $R^2$ and $R^3$ are both propionyloxy, namely 4,6α,9α-trifluoro-11β-hydroxy-16α-methyl-17α,21-dipropionyloxy-pregna-1,4-diene-3,20-dione.

52. The compound of claim 36 wherein $X^1$ is fluoro, $X^2$ is hydrogen, $X^3$ is chloro, $X^4$ is hydroxy, $R^1$ is hydrogen, $R^2$ and $R^3$ are both propionyloxy, namely 4-fluoro-9β-chloro-11β-hydroxy-16α-methyl-17α,21-dipropionyloxypregna-1,4-diene-3,20-dione.

53. A topical anti-inflammatory pharmaceutical composition which comprises a therapeutically effective amount of the compound of claim 1 in combination with at least one suitable pharmaceutical excipient.

54. A method of relieving a topical inflammatory condition in a mammal which comprises administering a therapeutically effective amount of the compound of claim 1 to said mammal.

* * * * *